United States Patent
Kuhn

(10) Patent No.: US 12,417,715 B2
(45) Date of Patent: Sep. 16, 2025

(54) EXTRUSION-BASED THREE-DIMENSIONAL PRINTED SOFT TISSUE MIMIC AND METHOD OF MANUFACTURE THEREOF

(71) Applicant: University of Connecticut, Farmington, CT (US)

(72) Inventor: Liisa Tiina Kuhn, West Hartford, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 665 days.

(21) Appl. No.: 17/729,172

(22) Filed: Apr. 26, 2022

(65) Prior Publication Data

US 2022/0343800 A1    Oct. 27, 2022

Related U.S. Application Data

(60) Provisional application No. 63/179,884, filed on Apr. 26, 2021.

(51) Int. Cl.
*G09B 23/30* (2006.01)
*A61F 2/50* (2006.01)
(Continued)

(52) U.S. Cl.
CPC ............ *G09B 23/30* (2013.01); *A61F 2/5046* (2013.01); *B33Y 80/00* (2014.12); *G09B 23/00* (2013.01)

(58) Field of Classification Search
CPC ... G09G 23/30; A61F 2/02; A61F 2/12; A61F 2/5046; A61F 2002/5047;
(Continued)

(56) References Cited

U.S. PATENT DOCUMENTS 4,592,755 A * 6/1986 Penton ...................... A61F 2/12
450/38
2017/0281367 A1    10/2017 Ketchum et al.
(Continued)

FOREIGN PATENT DOCUMENTS

| CN | 105997313 A | 10/2016 | |
| WO | 2013091720 A1 | 6/2013 | |
| WO | WO-2021043950 A1 * | 3/2021 | ........... A61F 2/0059 |

OTHER PUBLICATIONS

Caballar; "From a Personal Battle, One Company Created a Better Breast Prosthesis for All"; Breast Prosthesis: How 3D Technology Will Change Prosthetics; https://www.autodesk.com/redshift/breast-prosthesis/; Jan. 27, 2022, 10 pages.
(Continued)

*Primary Examiner* — Loren C Edwards
(74) *Attorney, Agent, or Firm* — CANTOR COLBURN LLP

(57) ABSTRACT

Disclosed herein is article comprising a first surface; and a second surface opposedly disposed to the first surface; where a space between the first surface and the second surface comprises a grid that comprises a plurality of first struts that have an average orientation in a first direction in a first plane with a first average spacing between neighboring first struts; and a plurality of second struts that have an average orientation in a second direction in a second plane with a second average spacing between neighboring second struts; where the first direction is different from the second direction; and where a portion of the plurality of first struts contact a portion of the plurality of second struts.

22 Claims, 17 Drawing Sheets

(51) Int. Cl.
  *B33Y 80/00* (2015.01)
  *G09B 23/00* (2006.01)
(58) Field of Classification Search
  CPC .............. A61F 2002/5049; A61F 2/52; A61F 2210/0076; A61F 2250/0023; A61F 2240/001; A61F 2240/002
  See application file for complete search history.

(56) References Cited

U.S. PATENT DOCUMENTS

2018/0228598 A1* 8/2018 Mathisen .................. A61F 2/12
2019/0125549 A1   5/2019 Park et al.

OTHER PUBLICATIONS

My Reflection; https://www.myreflection.co.nz; accessed Aug. 10, 2022, 12 pages.

Pearce; "Breast cancer survivors and others can use the Free Open Source 3D Customer to design and produce breast prosthetics"; Design and produce 3D printed, custom breast prosthetics; Opensource.com; Jul. 17, 2017, 10 pages.

Thomas;"Two Plymouth students create 3D printed PINK prosthetic breasts to help cancer survivors";https://www.3ders.org/articles/20180919-two-plymouth-students-create-3d-printed-pink-prosthetic-breasts-to-help-cancer-survivors.html;Sep. 19, 2018,11 pgs.

* cited by examiner

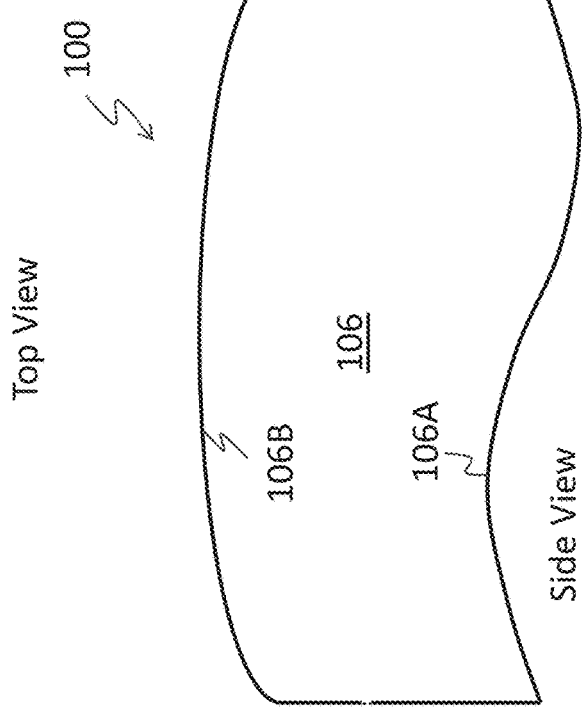
FIG. 1B
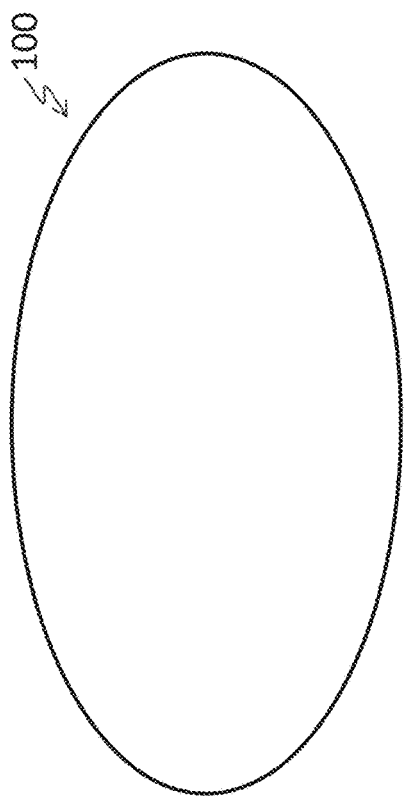
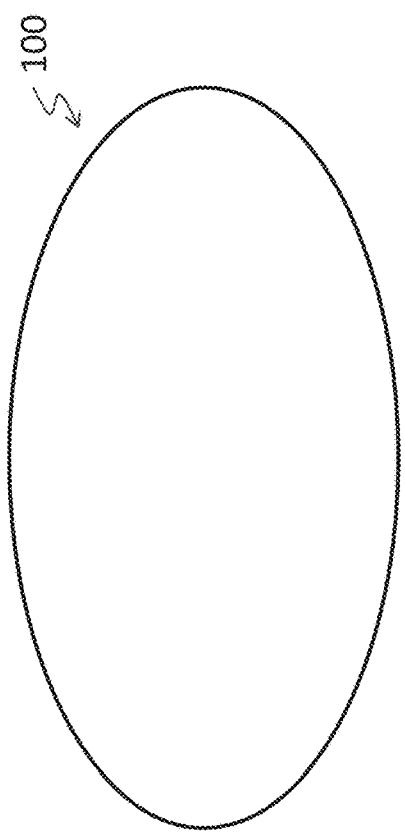
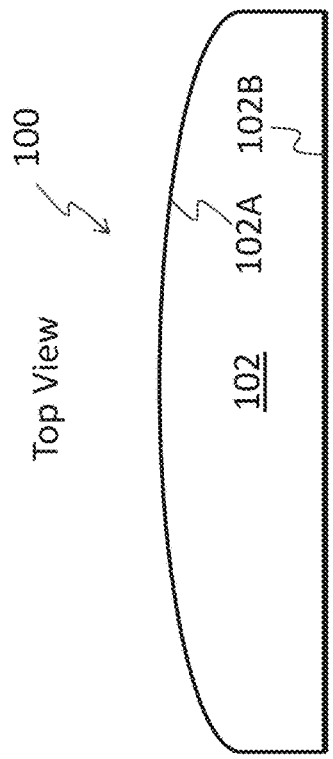
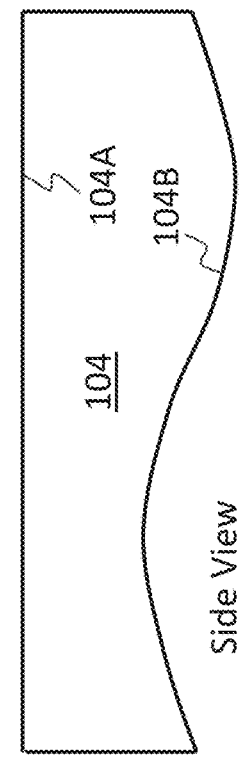
FIG. 1A

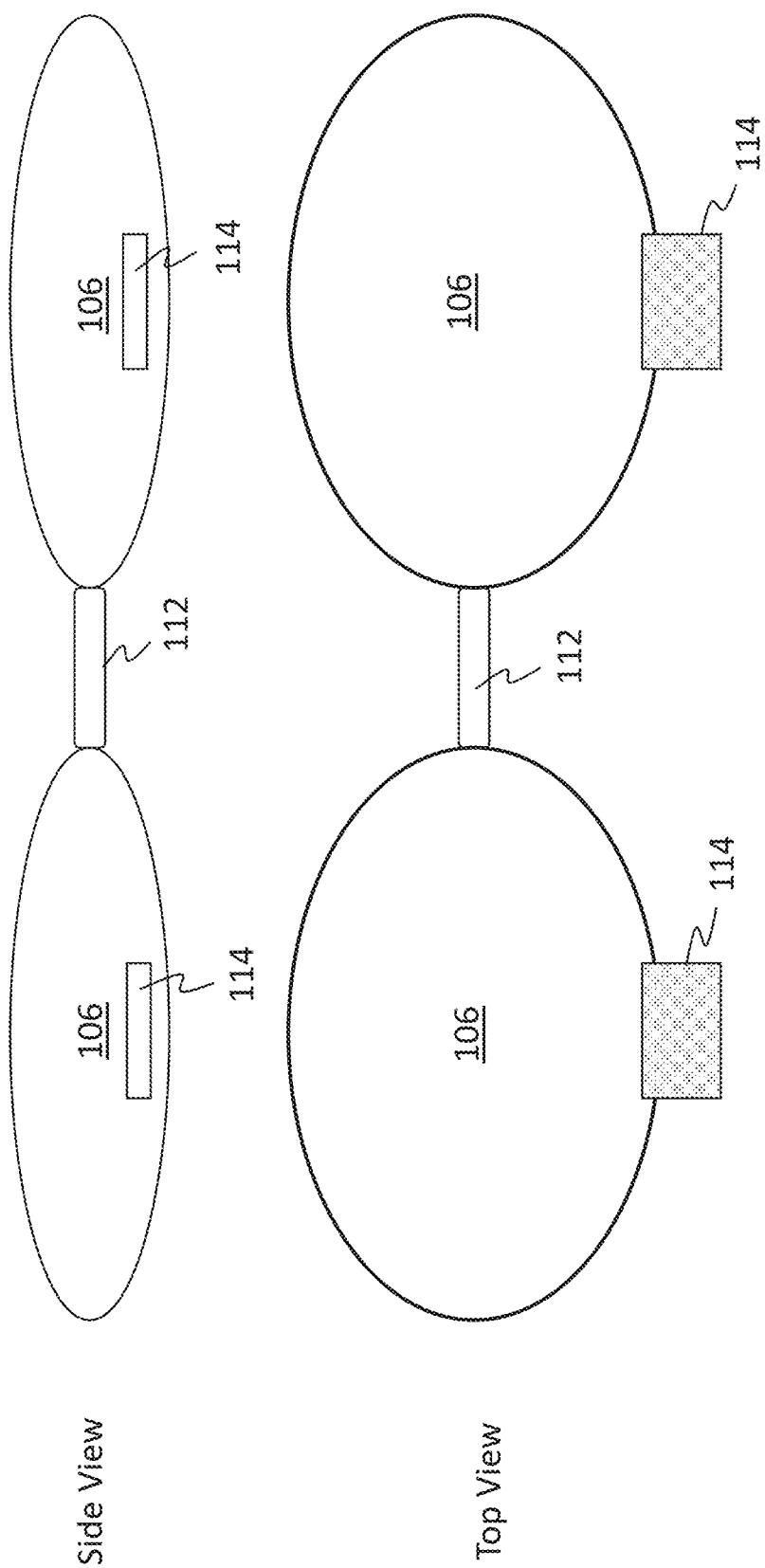

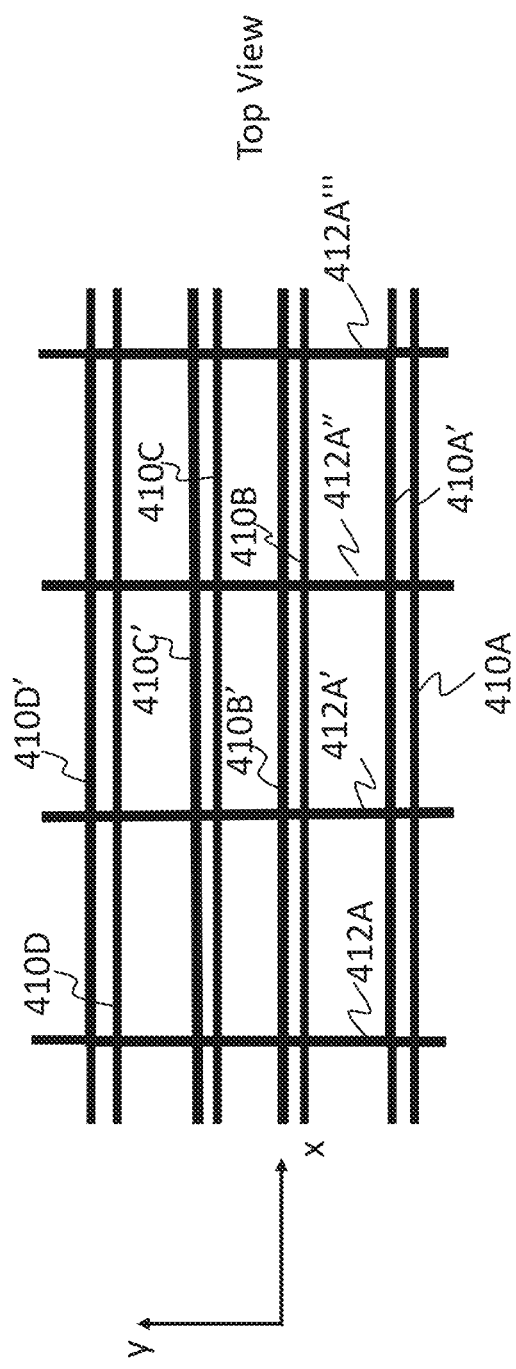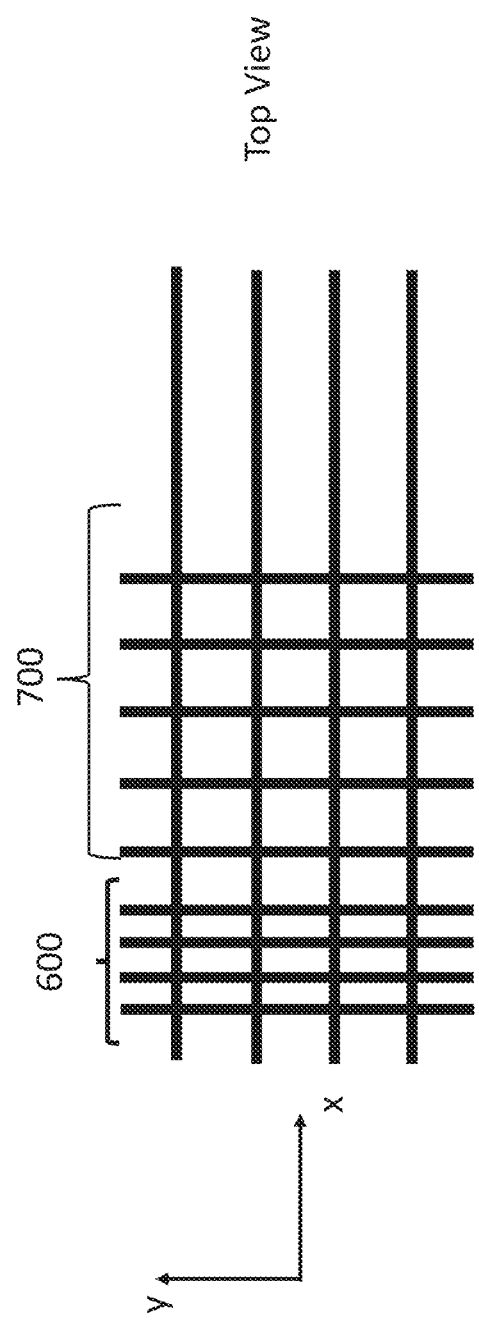

Top View

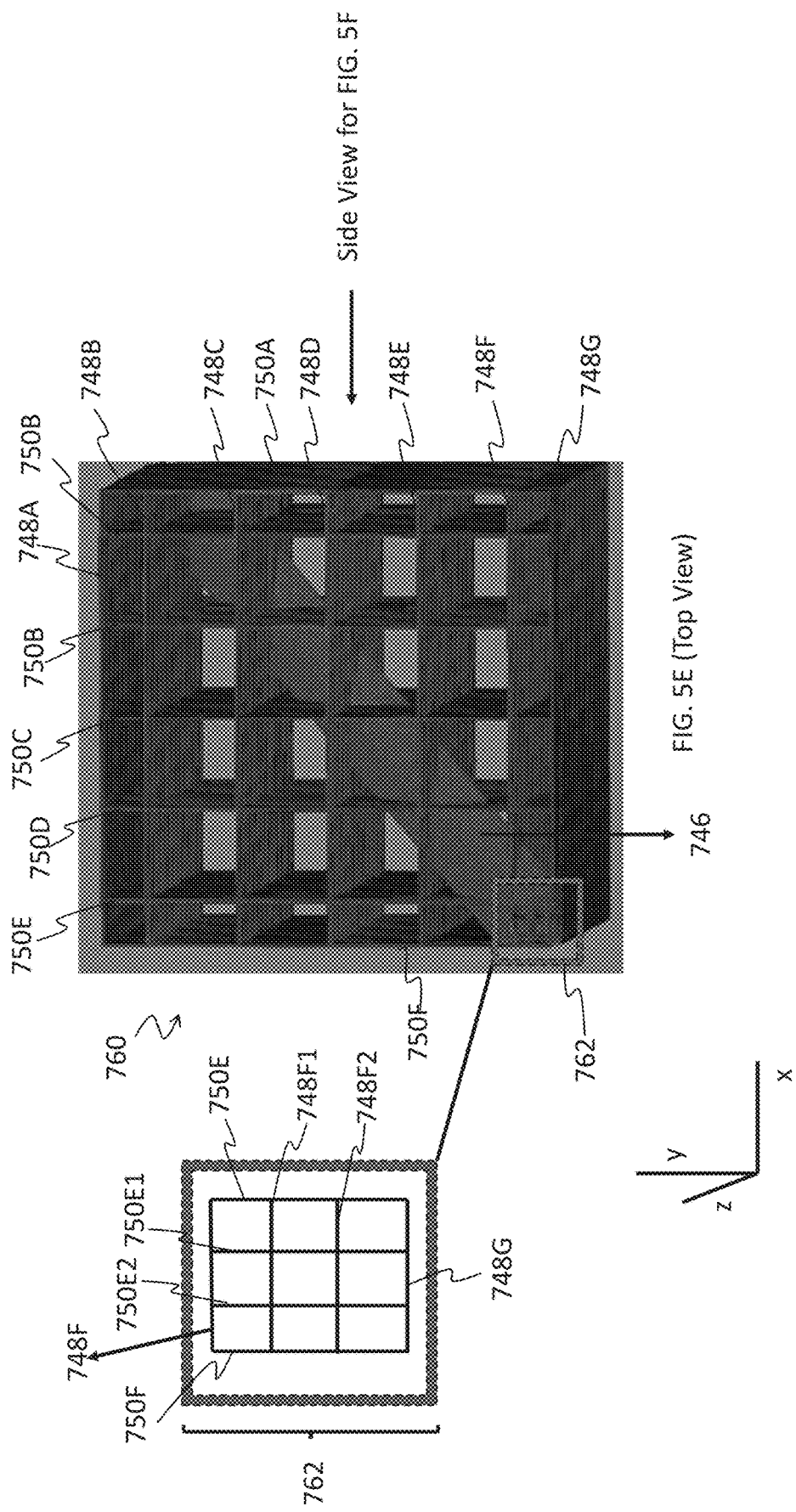

Top View

Top View

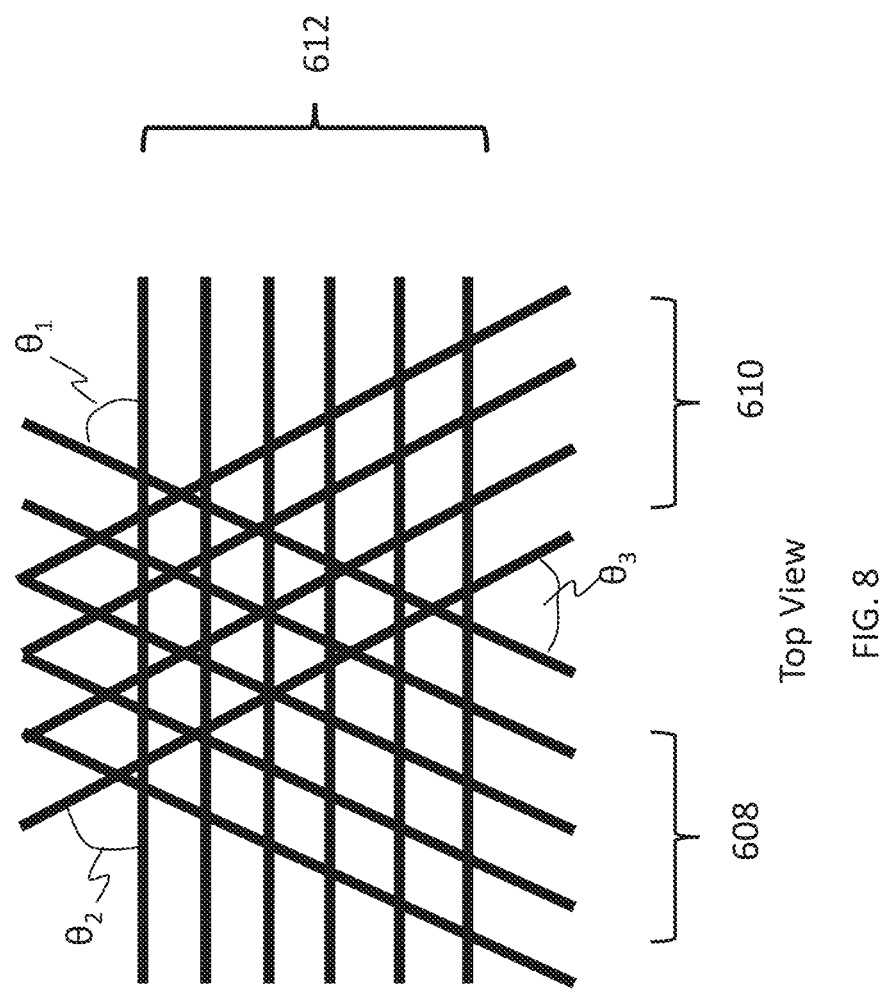

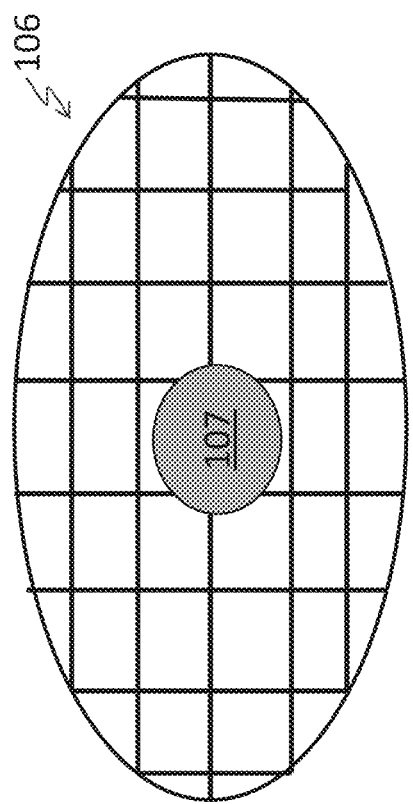
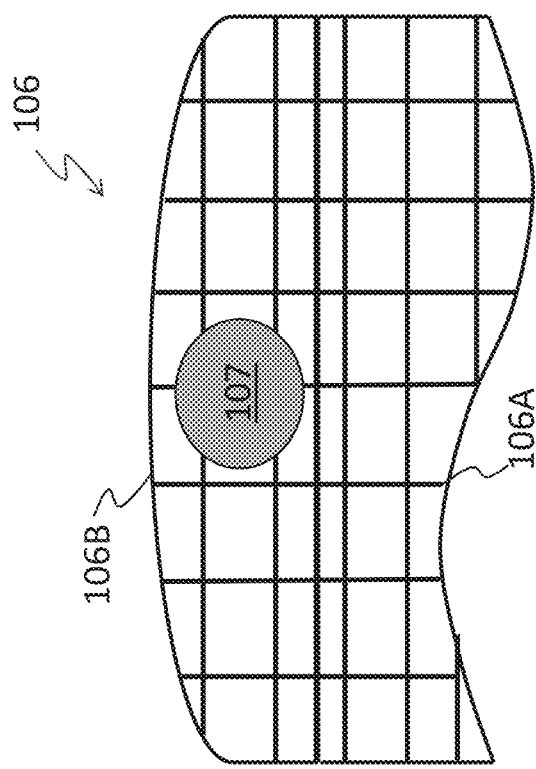
FIG. 9A

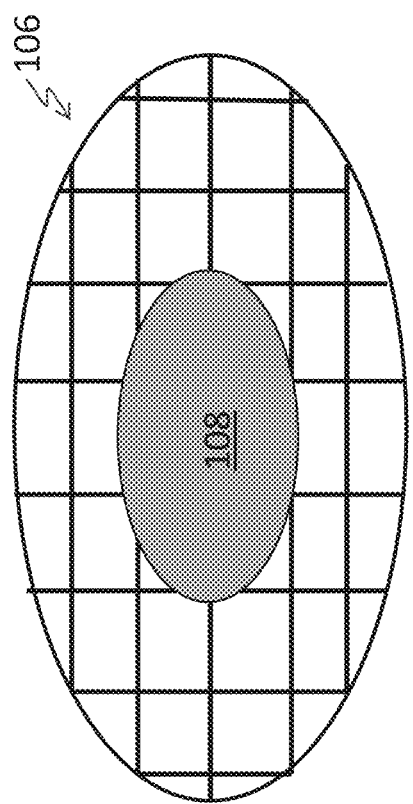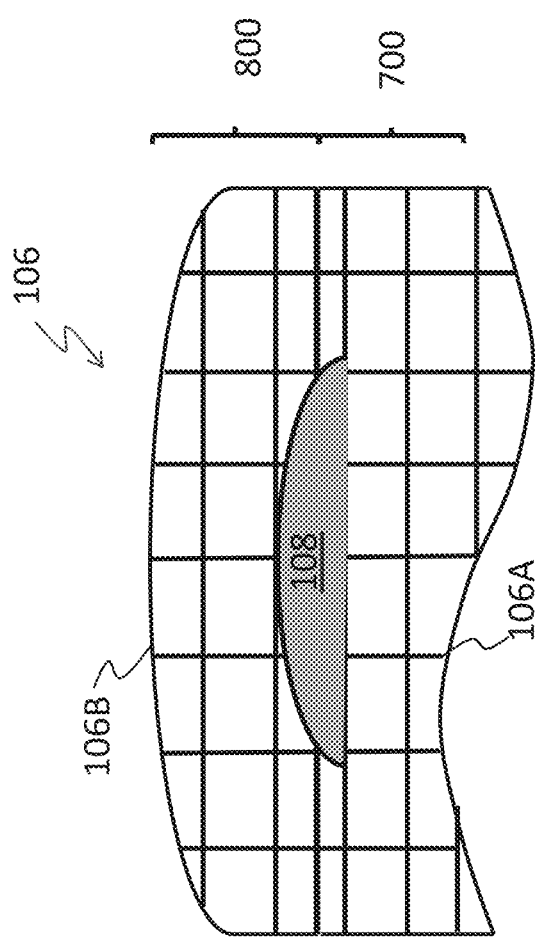
FIG. 9B

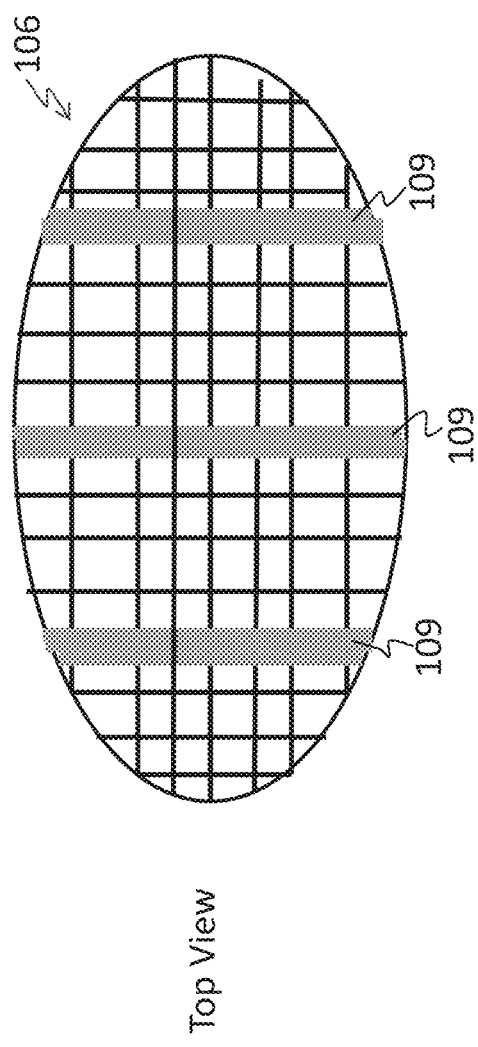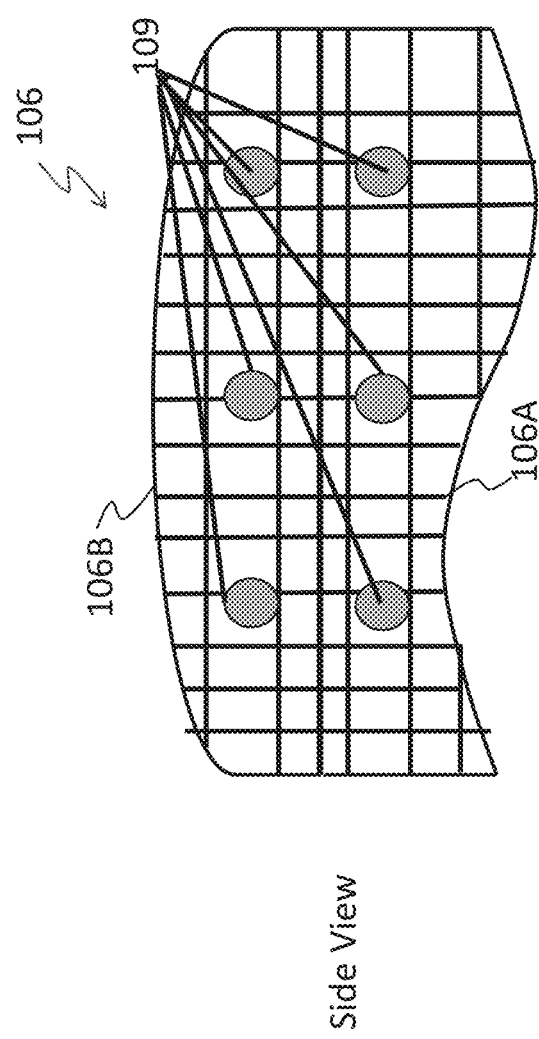
FIG. 9C

EXTRUSION-BASED THREE-DIMENSIONAL PRINTED SOFT TISSUE MIMIC AND METHOD OF MANUFACTURE THEREOF

CROSS-REFERENCE TO RELATED APPLICATIONS

This application claims priority to U.S. Provisional Application No. 63/179,884, filed Apr. 26, 2021, which is incorporated by reference in its entirety for all purposes.

FIELD OF THE DISCLOSURE

The invention described herein is directed to an extrusion-based three-dimensional printed soft tissue mimic or an augmentation that mimics a body part and method of manufacture thereof.

BACKGROUND OF THE DISCLOSURE

Surgery in the form of amputations are often performed on patients to remove portions of the body (e.g., limbs, breasts, and the like) that are wounded and damaged (e.g., soldiers who have received injuries on a battlefield) or diseased (e.g., gangrene, cancer, and the like). Even a small amount of tissue removed creates a deficit that causes physical deformity and can promote anxiety. When, for example, breasts are amputated it is often difficult to obtain satisfactory soft tissue mimics to compensate for the deficit.

In addition, existing soft tissue mimics are often heavy and worn in tight undergarments leading to pressure around and on the chest and on the shoulders. This pressure is often a source of pain at the breast surgery site in many users, which may become very fatiguing and taxing as the day wears on. Straps and bands, while managing weight, volume and position of soft tissue mimics, cause significant discomfort and often, pain, especially in post-surgical situations.

Commercially available soft tissue mimics that are presently used as replacements for amputated body parts are often non-porous solids. A 3D printer may be used to create the mold which serves as a negative image (a template) for the amputated body part. A molten polymer is then poured into the mold to form the soft tissue mimic. After the molten part has solidified, the mold is removed and the soft tissue mimic is supplied to the patient. These non-porous, solid, soft tissue mimics are heavy and do not breathe (they do not allow a fluid to travel through them). This often produces sweat buildup, which is a discomfort to the patient.

Previous additive manufacturing techniques, such as that described in U.S. Patent Application Publication No. 2014/0163445 use rigid free-form structures to produce a lattice structure that is impregnated by a polymeric material, a ceramic or a metal. The lattices are manufactured using 3D printing and are then coated with the polymer, ceramic or a metal. The lattice is however, rigid and cannot move. Because of the rigid lattice it does not account for the natural movement of the users missing body part, let alone provide a desired aesthetic appearance.

In addition, there are readily available (i.e., "off-the-shelf") body parts that are made from solid silicone (polysiloxane), knitted materials, foam, or a bag with microbeads. The readily available body parts may be made by casting an elastomeric material like silicone or a polyurethane into a mold to form a solid form. Current readily available body parts are expensive, uncomfortable (e.g., too stiff/hard against a patient's skin or solid and sweat inducing), poor fitting against a patient's skin, do not stay in place, provide little resemblance to the body part that is being mimicked, and other well-known disadvantages. Moreover, traditional soft tissue mimics are heavy and dense, and thus the patient may have to wear tight clothing, use straps, and/or use adhesive to properly use and retain the soft tissue mimic with their body.

With regard to breast prostheses, some of the molds used to produce breast prostheses are personalized to the patient by creating a mold for silicone based on a 3D scan of the patient. These breast prostheses overcome the issues of being poor fitting because they have a surface that matches the chest wall structure after surgery. However, they are dense and do not promote breathability.

Based on the foregoing, a need exists for a breathable, low cost, lightweight, and porous three-dimensional (3D) soft tissue mimic that mimics a missing body part and the method of creating the same.

SUMMARY OF THE DISCLOSURE

Disclosed herein is article comprising a first surface; and a second surface opposedly disposed to the first surface; where a space between the first surface and the second surface comprises a grid that comprises a plurality of first struts that have an average orientation in a first direction in a first plane with a first average spacing between neighboring first struts; and a plurality of second struts that have an average orientation in a second direction in a second plane with a second average spacing between neighboring second struts; where the first direction is different from the second direction; and where a portion of the plurality of first struts contact a portion of the plurality of second struts.

Disclosed herein is a method of manufacturing a soft tissue mimic comprising scanning a portion of a patient's body with an imaging device; transferring one or more images of the patient's body to a processor; creating an image of the soft tissue mimic using the processor; extruding from a nozzle of a 3D printer a soft tissue mimic that approximates the image created in the processor; wherein the soft tissue mimic comprises a first surface that contacts the user's body; and a second surface opposedly disposed to the first surface; where a space between the first surface and the second surface comprises a grid that comprises a plurality of first struts that have an average orientation in a first direction in a first plane with a first average spacing between neighboring first struts; and a plurality of second struts that have an average orientation in a second direction in a second plane with a second average spacing between neighboring second struts; where the first direction is different from the second direction; and where a portion of the plurality of first struts contact a portion of the plurality of second struts.

BRIEF DESCRIPTION OF THE DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various features, steps and combinations of features/steps described below and illustrated in the figures can be arranged and organized differently to result in embodiments which are still within the scope of the present disclosure.

Figure 2:
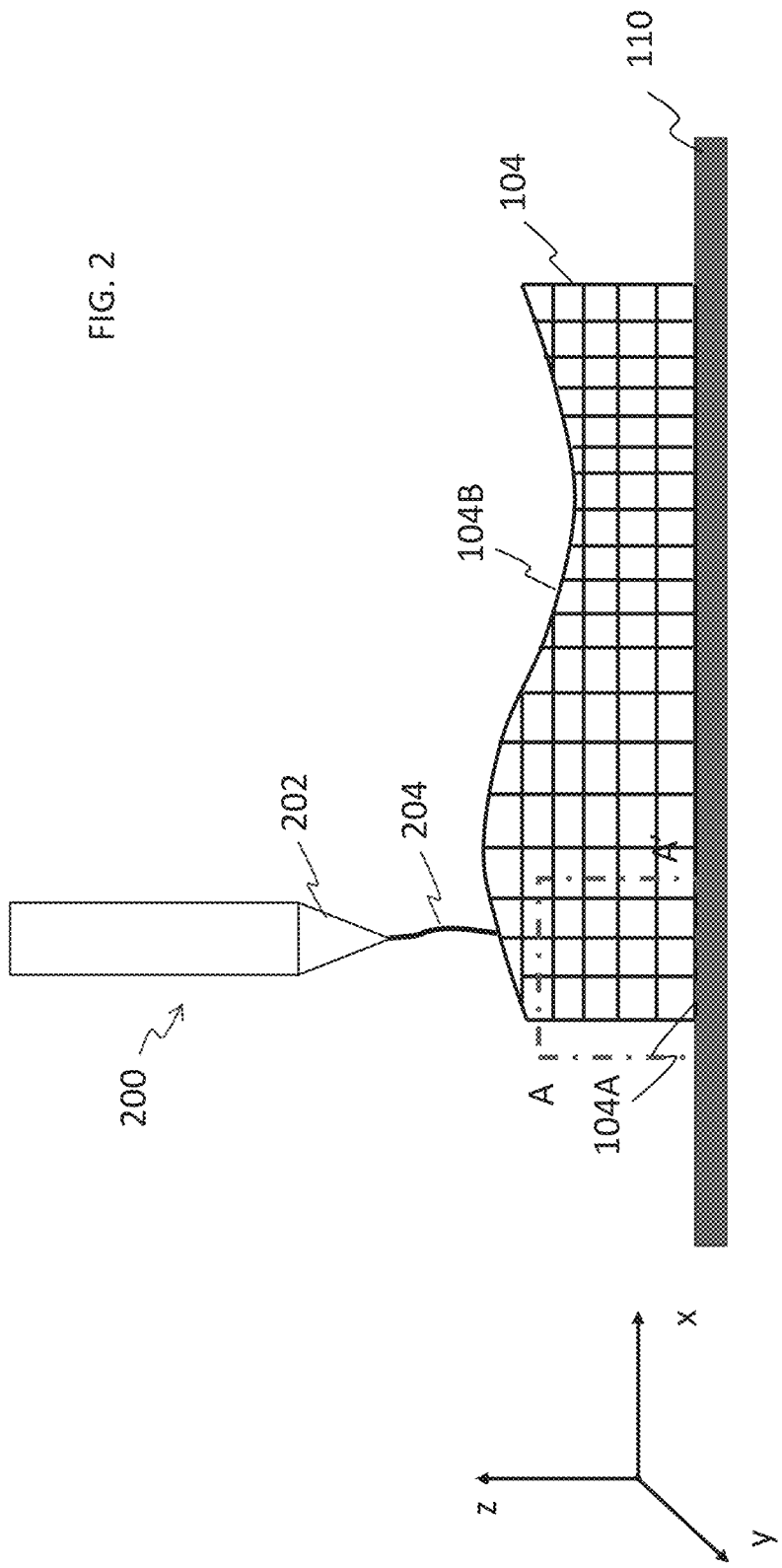
Figure 3:
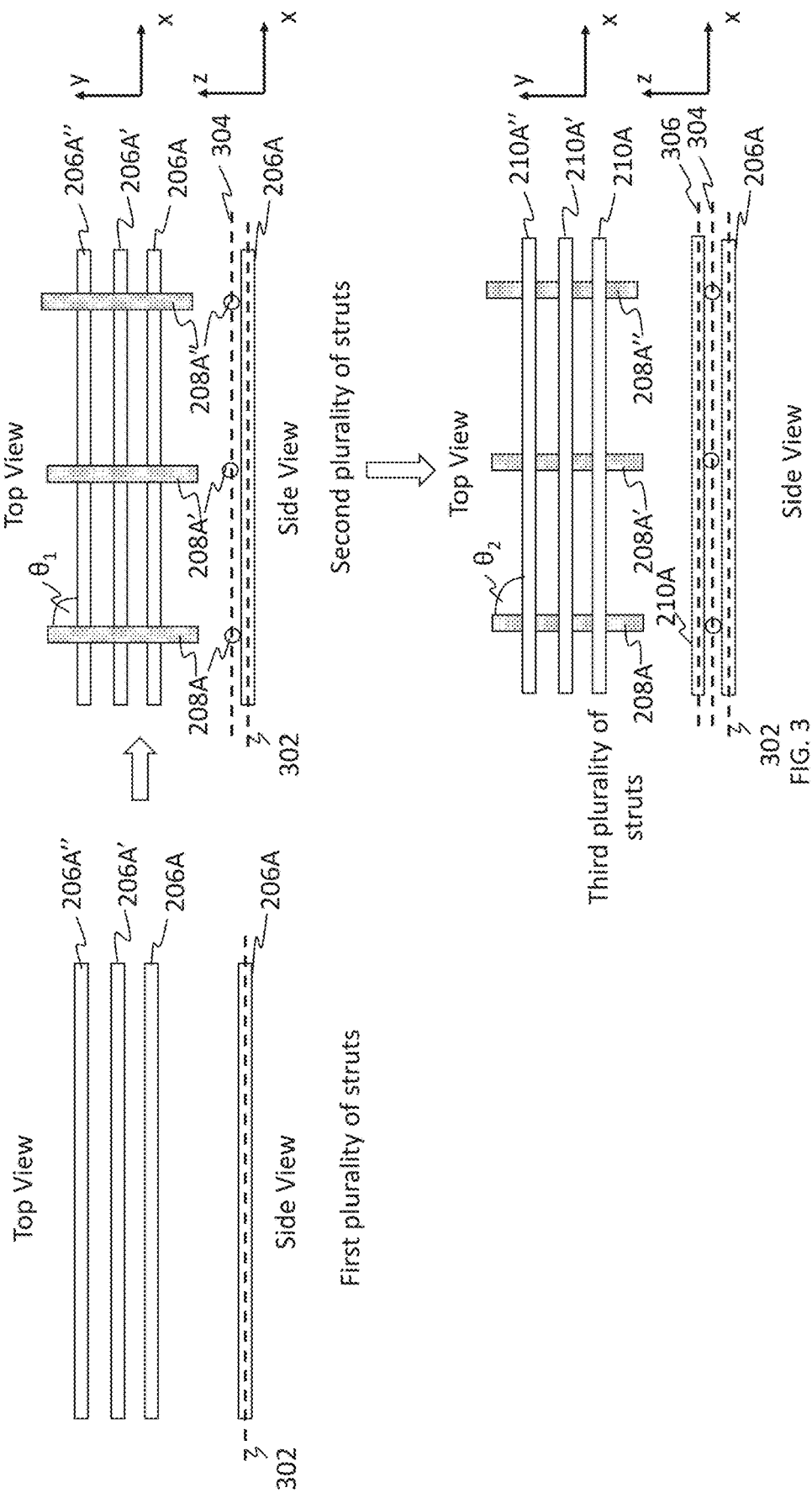
Figure 4:
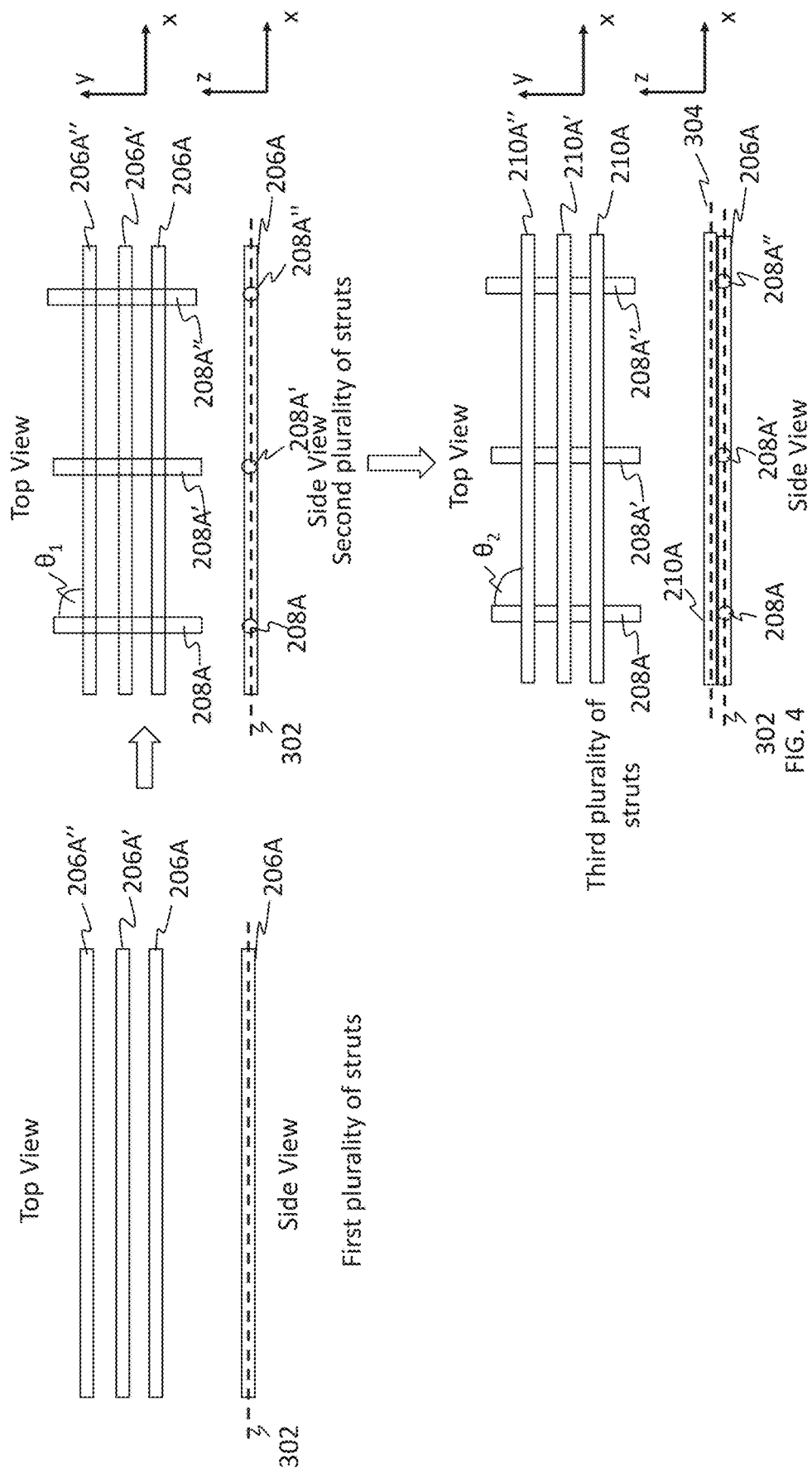
Figure 5D:
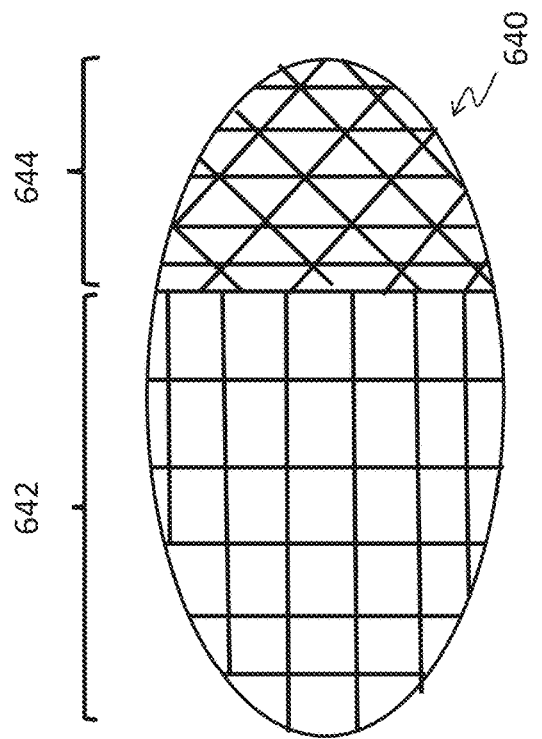
Figure 5C:
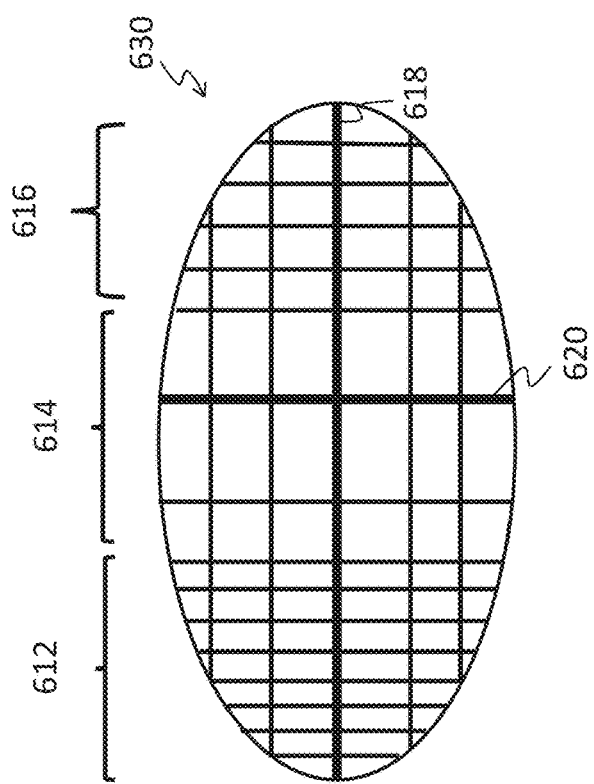
Figure 5F:
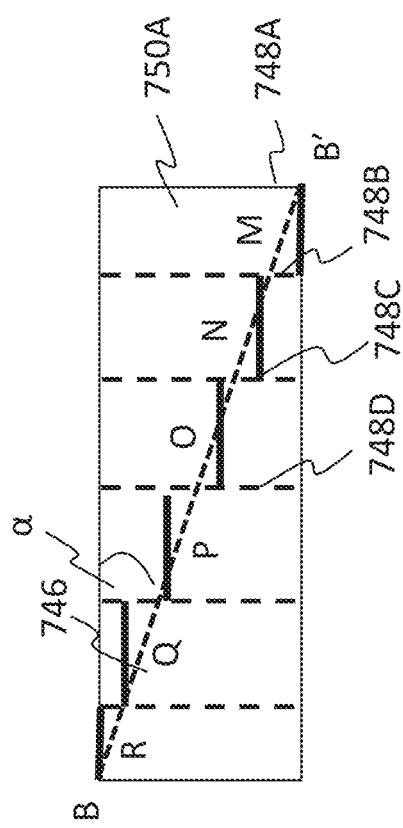
Figure 5G:
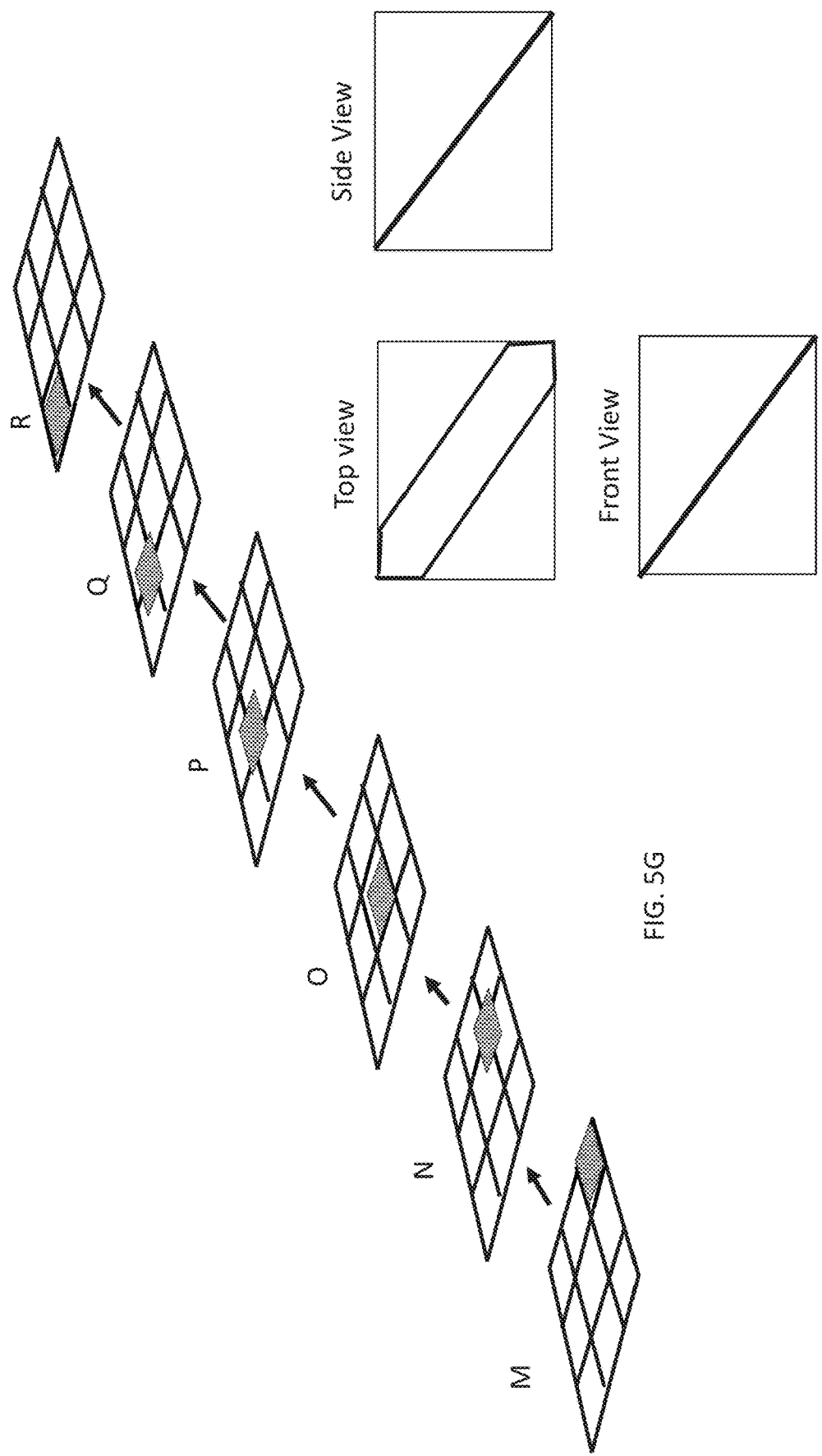
Figure 7:
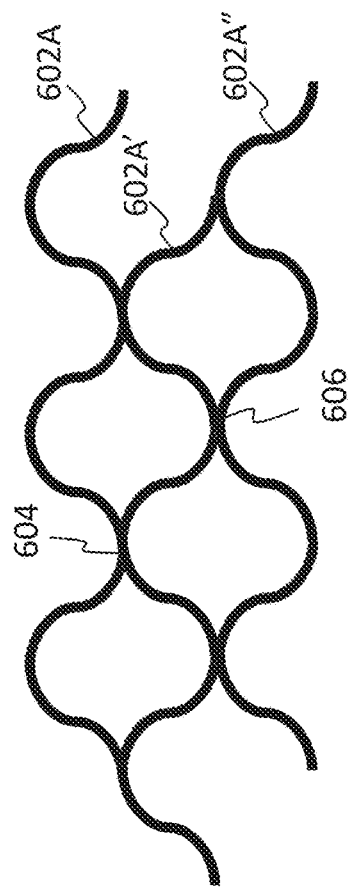
Figure 6:
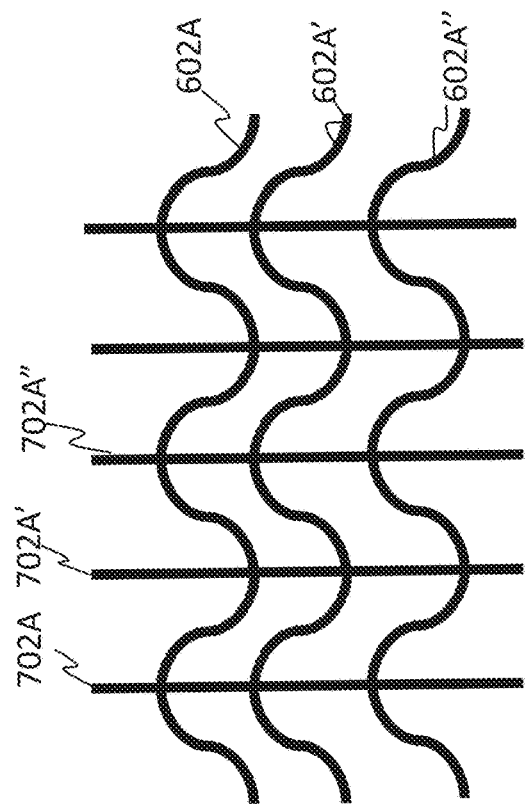
Figure 9D:
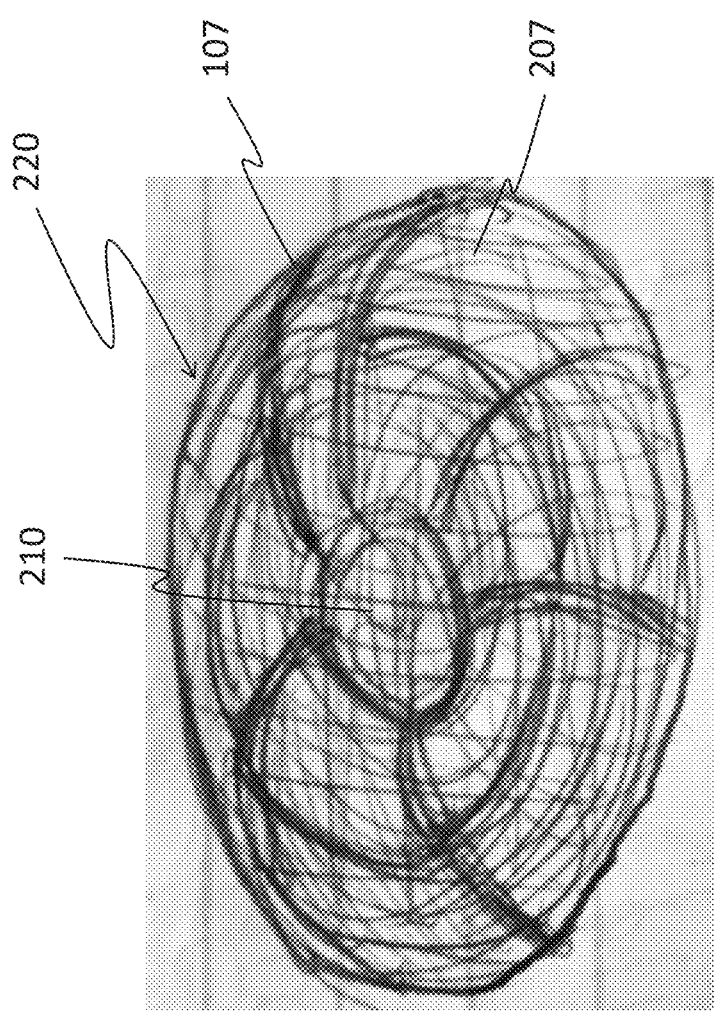
Figure 10:
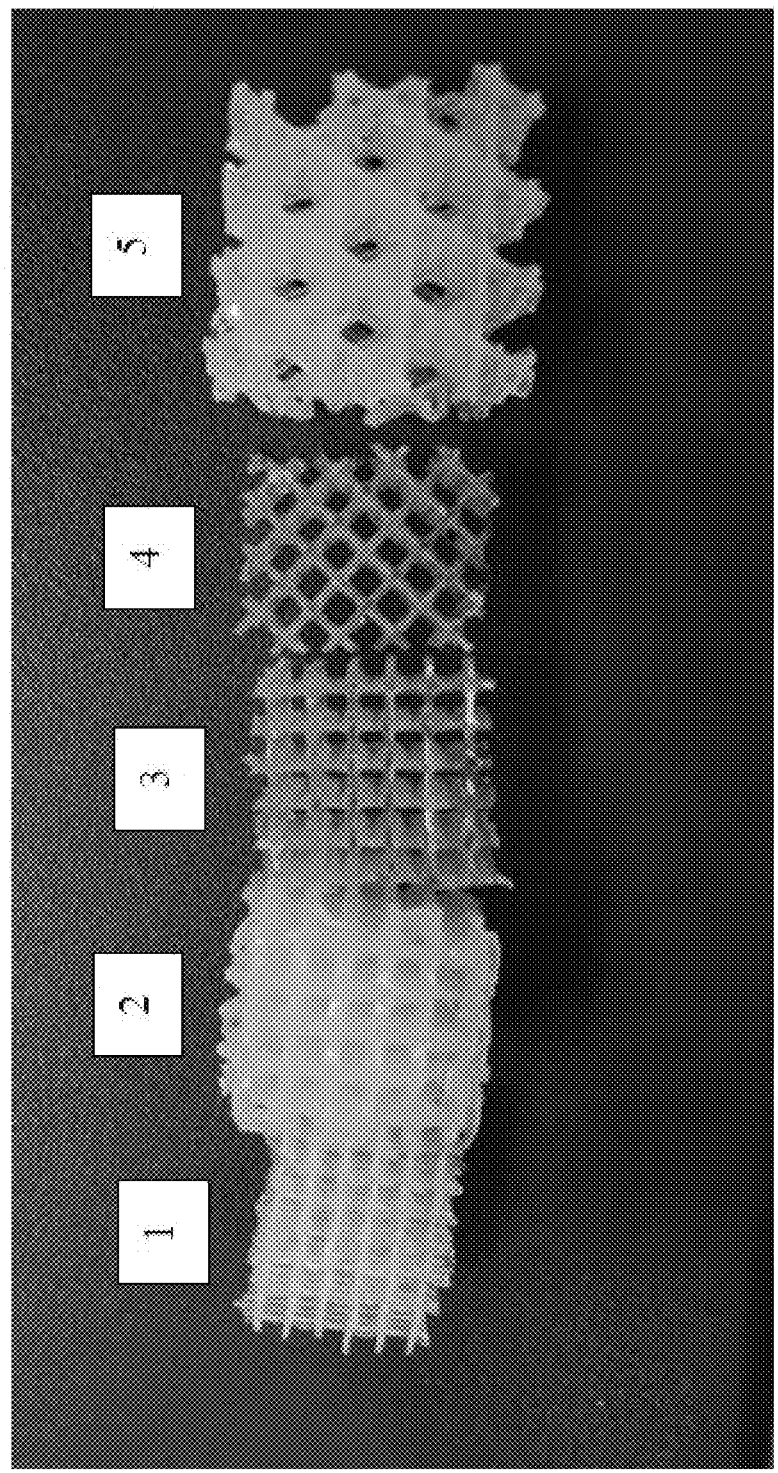

To assist those of ordinary skill in the art in making and using the disclosed assemblies, systems and methods, reference is made to the appended figures, wherein:

FIG. 1A depicts an exemplary two-piece soft tissue mimic;

FIG. 1B depicts an exemplary single-piece soft tissue mimic;

FIG. 1C depicts two or more soft tissue mimic sections held together by a connecting piece;

FIG. 2 depicts an exemplary method of manufacturing the soft tissue mimic using a 3D printer;

FIG. 3 depicts an exemplary method of manufacturing the soft tissue mimic with a bridging grid structure;

FIG. 4 depicts an exemplary method of manufacturing the soft tissue mimic with a non-bridging grid structure;

FIG. 5A depicts a top view of an exemplary strut layer where the struts have different spacings between different struts in the layer;

FIG. 5B depicts a top view of an exemplary strut layer where there is a higher strut density in one region when compared with another region;

FIG. 5C depicts a top view of an exemplary soft tissue mimic where there is a higher strut density in one region when compared with another region;

FIG. 5D depicts a top view of an exemplary soft tissue mimic where one region of the soft tissue mimic has a different strut configuration from another region of the soft tissue mimic;

FIG. 5E depicts an exemplary soft tissue mimic where a controlled deposition pattern results in the formation of a dense larger strut in a different plane in the soft tissue mimic;

FIG. 5F is a side view of FIG. 5E;

FIG. 5G depicts another view of the manufacturing of the grid of FIG. 5E and FIG. 5F;

FIG. 6 depicts a top view of an exemplary strut layer where one plurality of struts includes wavy (sinusoidal) struts;

FIG. 7 depicts a top view of an exemplary strut layer where the struts are wavy struts that contact one another at specific points;

FIG. 8 depicts a top view of an exemplary grid formed by three different pluralities of struts, where each plurality of struts is oriented in different directions;

FIG. 9A depicts a top view and a side view of an exemplary soft tissue mimic that contains an area of dense elastomer or an area of different elastomer;

FIG. 9B depicts a soft tissue mimic that comprises two regions that have a similar structure but contain two different materials of construction;

FIG. 9C depicts a soft tissue mimic that has pores or channels extending through the volume of the soft tissue mimic for removal of fluids;

FIG. 9D depicts an exemplary soft tissue mimic where the dense struts within the grid structure provide bridge-like reinforcement; and FIG. 10 is a photo that shows various examples of the soft tissue mimics produced using 3D extrusion direct write printing. The grid pattern of the soft tissue mimics are visible.

DETAILED DESCRIPTION OF THE DISCLOSURE

Disclosed herein is a soft tissue mimic and a method for manufacturing the soft tissue mimic that may be utilized externally, internally, or combinations thereof to a patient's body so as to recreate and/or supplement a missing portion of the patient's body. In an exemplary embodiment, the soft tissue mimic is manufactured via extrusion-based direct ink write 3-dimensional (3D) printing. In direct ink write manufacturing, the liquid-phase ink is dispensed out of small nozzles at controlled flow rates and deposited along digitally defined paths to fabricate 3D structures layer-by-layer. The soft tissue mimic is also sometimes referred to as a prosthetic and generally mimics a body part that may or may not have been removed. It is to be noted that while this document refers to the soft tissue mimic as being developed for a "patient", it may be developed for a user who is not sick (or has undergone an amputation) and just wants to enhance or change his/her appearance.

In an embodiment, the soft tissue mimic may be used to restore symmetry and improve aesthetics of the patient's body. When the soft tissue mimic is used internally in a patient's body, it is understood that the material will be of medical quality (e.g., medical grade silicone) and be compatible with the patient's body. The soft tissue mimic described herein may provide a low cost, breathable, lightweight, porous article that gently interfaces with the patient's skin topography and is personalized to the patient's shape/features/skin.

In an embodiment, the soft tissue mimic includes a lattice structure that may be utilized as a clothing insert to restore appearance of soft tissues such as biceps, legs, buttocks, breasts, and the like. The soft tissue mimic can be used directly against the skin, outside of clothing, as well as inside of clothing, depending upon the desires of the patient. It may also be used during active activities (e.g., running, swimming, and the like).

The method comprises scanning a portion of the patient's body with an imaging device such as a scanner, a camera, or the like, numerous times to develop a 3D image of the portion that is to be replaced. The plurality of scans may be taken in a plurality of different positions. The scans (or images) are transferred to a microprocessor (hereinafter processor) that contains 3D modelling software, where the image can be manipulated to create an object file of the soft tissue mimic that is desired. The image is then transferred in numerical form to a 3D printer that produces the customized soft tissue mimic as detailed below.

The scan may include acquiring shape, volume, and/or weight data of the portion of the patient for which the soft tissue mimic is to be developed. The customized soft tissue mimic may then be developed that is adjusted to the shape, volume, and/or weight of the imaged portion using additive manufacturing or 3D manufacturing.

In one embodiment, an image of soft tissue mimic may be generated from a portion of the body that has not been amputated. For example, if the patient has already had a left leg or left breast amputated, an image of unamputated right leg or right breast may be scanned into a processor. The image of the right leg or breast is used by the processor to create a symmetrical image of the missing left leg or left breast. The symmetrical image can be a mirror image. The image of the left leg or left breast is fed as an object file to the 3D printer to create the soft tissue mimic.

In another embodiment, the exterior design of the soft tissue mimic may be based, at least in part, on a 3D scan or image of the patient's intact body part (e.g., a breast, a calf, a thigh, and the like), which can be taken with an optical scanner. The data is mirror imaged and matched up with another 3D image of the patient's misshapen body (which typically happens after surgery such as a mastectomy) part to create the object file of the soft tissue mimic. The soft tissue mimic has an anterior exterior surface that replicates an existing or desired body part and a posterior exterior shape or surface that matches the deformed surface of the user's body after surgery.

The production of the soft tissue mimic may involve creating a 3D printed "support structure" that matches the shape of the deformed body region to be used as a base for 3D printing rather than a flat stage. The disclosed 3D printing process involves conformal or contour 3D printing on the support structure. By using this process and keeping the material properties and the print parameters in a narrow range it is possible to create a highly desirable soft tissue mimic with superior performance and personalization over conventional "off-the-shelf" body parts.

In another embodiment, the method comprises receiving, from a scanner, a first 3D scan (or a plurality of first scans) of at least a portion of the user in a first position (such as for example, a relaxed position). The portion of the user that is scanned includes the portion that is to replaced (e.g., a breast, a limb, and so on) and for which the soft tissue mimic is to be developed. The first 3D scan is preferably taken prior to surgery with the existing body part in its normal position.

The method further comprises receiving, from the scanner, a second 3D scan (or a plurality of second scans) of the same portion of the user in a second position (such as for example, a position where the deformed portion of the body after surgery is imaged). The imaging or scanning can be performed by an optical scanner or a camera and the images obtained may be mapped using a processor where one or more translation matrices corresponding to the first and second 3D scans may be prepared.

In an embodiment, the collected images are analyzed using a processor that contains 3D modelling software. The images may be subdivided into matrices. Analyzing the one or more matrices may comprise warping or modifying the one or more matrices using a least-squares regression method. The method may further comprise analyzing the one or more matrices to identify regions of the user having scar tissue and adjusting the density and shape of the structure based on the identified regions of the user. Data obtained from the scans and images is then transferred to an extrusion-based direct write 3D printer for manufacturing. This method permits manufacturing customized a soft tissue mimic for the user.

In an embodiment, the soft tissue mimic may be manufactured by an extrusion-based direct write 3D printer using an organic polymeric elastomer (hereinafter polymeric elastomer). The polymeric elastomer may comprise a thermoplastic polymer, a blend of thermoplastic polymer, a thermosetting polymer, or a blend of a thermoplastic polymer with a thermosetting polymer. The polymer elastomer may also comprise a blend of polymers, copolymers, terpolymers, or combinations comprising at least one of the foregoing organic polymers. The organic polymer can also be an oligomer, a homopolymer, a copolymer, a block copolymer, an alternating block copolymer, a random polymer, a random copolymer, a random block copolymer, a graft copolymer, a star block copolymer, a dendrimer, an ionomer, or the like, or a combination thereof. The polymeric elastomer may have a number average molecular weight of greater than 10,000 grams per mole, preferably greater than 20,000 g/mole up to a value of 2,000,000 g/mole as determined using gel permeation chromatography. In one exemplary embodiment, the polymeric elastomer has a number average molecular weight of 30,000 to 60,000 g/mole as determined using gel permeation chromatography. In another exemplary embodiment, the polymeric elastomer has an average molecule weight of 750,000 to 1,500,000 g/mole as determined by gel permeation chromatography.

The polymeric elastomer is preferably a crosslinked elastomer and is preferably one that does not react with or swell upon being contacted with bodily fluids. It is preferably one that does not agitate the skin upon contacting it. It is further one that can be washed with water and/or alcohol (for purposes of cleaning it) while preferably not absorbing water or alcohol. It is preferably one that does not undergo dimensional distortion, degradation or a change in physical properties with temperature changes between −30° C. to 300° C., preferably −20 to 150° C. and preferably −10° C. to 60° C.

The polymeric elastomer is one that can be activated to undergo crosslinking but can be extruded before or during the activation (i.e., one where the crosslinking is initiated) but that undergoes crosslinking at a rate effective to permit gelation only after it is extruded to form the grid or a lattice that eventually forms the soft tissue mimic. In an exemplary embodiment, the cross-linking may be initiated by the presence of moisture (for example by moisture present in the atmosphere) and the cure rate is sufficiently slow that it does not cure in the nozzle prior to extrusion. An example of such an elastomer is a room temperature vulcanizate. Examples of such room temperature vulcanizates are silicone elastomers and silanized polyurethane elastomers.

The polymeric elastomer is one that can preferably maintain its filament shape after extrusion while it undergoes curing without excessive distortion. The filament after extrusion is referred to as a strut. The strut may be linear, curved, wavy, and is preferably a 1-dimensional structure (i.e., its mass is proportional to its length). In an embodiment, the filament may be cured to form the strut by using radiation (e.g., UV radiation, infrared radiation, and the like) or heat (e.g., by raising the temperature through convection).

Examples of polymeric elastomeric materials include polybutadienes, polyisoprenes, styrene-butadiene rubber, poly(styrene)-block-poly(butadiene), poly(acrylonitrile)-block-poly(styrene)-block-poly(butadiene) (ABS), polychloroprenes, epichlorohydrin rubber, polyacrylic rubber, silicone elastomers (polysiloxanes), polyurethanes, silanized polyurethanes, thermoplastic polyurethanes, fluorosilicone elastomers, fluoroelastomers, perfluoroelastomers, polyether block amides (PEBA), chlorosulfonated polyethylene, ethylene propylene diene rubber (EPR), ethylene-vinyl acetate elastomers, nitrile elastomers, or the like, or a combination thereof. Preferred elastomers are those that do not react with the human body i.e., those that are biocompatible. Exemplary elastomers are polysiloxanes or fluorine containing elastomers (e.g., fluorosilicone elastomers, fluoroelastomers, perfluoroelastomers, and the like), polyurethanes, or a combination thereof.

In a nonlimiting example, the soft tissue mimic described herein may be manufactured by an extrusion laminar flow 3D bioprinter. Although examples described herein may reference a particular 3D printer (e.g., an extrusion laminar flow 3D bioprinter), it should be appreciated that the method of creating the soft tissue mimic, as outlined below, can be accomplished by alternative 3D printers, as understood by a person skilled in the art. An example of the extrusion laminar flow 3D bioprinter includes The BioassemblyBot® manufactured by Advanced Solutions Life Sciences, LLC (Louisville, KY). Details of the soft tissue mimic and the manufacturing of the soft tissue mimic are discussed below.

The 3D printing parameters that may be useful to control include temperature, nozzle size, pressure and print head speed, which control the filament size. The following is a table outlining print parameters for several elastomeric materials. It should be understood that the Table 1 below is a non-exhaustive list compiled for ease of teaching a person skilled in the art and is not intended to be limiting. It should also be understood that the desired print parameters may depend on a variety of print conditions, including filament material, filament size, soft tissue mimic design, printing environment (e.g., humidity, temperature, and the like), needle size, needle orientation, bioprinter, bioprinter head speed. Based thereon, as an example, the following table outlines the print parameters using a rectilinear print pattern and a 22 G (ID 0.413 mm) needle. It is to be noted that the Dowsil™ SE1700/Sylgard™ 184 material required a 20 G (ID 0.603 mm) needle due to higher viscosity.

TABLE 1

| Silicone Product Name | Bioprinter | speed | Filament spacing (between edges of filaments) | Pressure (kPa) | Filament diameter (mm) |
|---|---|---|---|---|---|
| PCI Silcoferm ® | EnvisionTEC 3D Bioplotter | 15 mm/sec | 1.0 mm-1.7 mm | 290 kPa | 0.320 mm |
| | Cellink ® BioX | 5 mm/sec | 1.0 mm-3.0 mm | 250 kPa | 0.3 mm-1.0 mm |
| OSI Quad ® Max | Cellink ® BioX | 5 mm/sec | 1.0-4.0 mm | 170 kPa | 0.3 mm-0.5 mm |
| | BioAssemblyBot ® | 5-80 mm/sec | 1.5 mm-5.0 mm | 172-551 kPa | 0.2 mm-1.3 mm |
| 4:1 mix Dowsil™ SE1700 Sylgard™ 184 | BioAssemblyBot ® | 35 mm/sec | 2.0 mm-4.0 mm | 137 kPa | Was more of a tape than a round cross section 0.3 mm thick, 1 mm or more wide. |
| Aqueon ® | Cellink ® BioX | 5-10 mm/sec | 1.0 mm-3.0 mm | 250 kPa | 0.7 mm-1.2 mm |
| Loctite Clear | Cellink ® BioX | 5-10 mm/sec | 0.5 mm-1.4 mm | 250 kPa | 1.0 mm-2.0 mm |

In an embodiment, the soft tissue mimic is made by extrusion of the elastomer through needles or nozzles ranging from 18 gauge-22 gauge and applying pressures from 100 kPa-650 kPa, more preferably 300 to 600 kPa using a speed of 5-90 mm/sec, more preferably 35-80 mm/sec.

In an embodiment, the material of the soft tissue mimic may comprise an elastomeric material made of silicone rubber (a polysiloxane), that may cure by a platinum-catalyzed cure system, a condensation cure system, a peroxide cure system, or an oxime cure system. The silicone rubber used to make the soft tissue mimic may be formulated as a one part or a two-part formulation. The formulation may or may not use an ultraviolet initiated curing reaction. The material properties that may be important to control include, but are not limited to, viscosity, pot life, cure time, hardness, tensile strength, elongation at break, tear strength, shrinkage. Use of a UV curable material may promote more complex soft tissue mimic structures because the elastomeric material may be cured soon after application to form the lattice structure and allowing larger self-supporting overhangs.

Materials that may be used include thermosetting or thermoplastic formulations of silicone rubber or polyurethane based materials. The following table (Table 2) is a non-exhaustive list of elastomers that have been printed into a lattice structure, as described herein.

TABLE 2

| Product Name | Shore hardness A | Elongation at break | Tensile strength and tear strength of fully dense material | Compressive modulus of a 3D bioprinted part with rectilinear infill unless noted |
|---|---|---|---|---|
| 4:1 mix Dowsil™ SE1700 Sylgard™ 184 | 43 Shore A | 100% | 4 MPa and 3.7N/mm | Not rectilinear; is a 60,60,60 degree pattern. In z-direction 7189 Pa. In x-y direction: 6733 Pa Strut thickness 1 mm. |
| PCI Silcoferm s ® | 20 Shore A | Up to 25% of joint width | 0.9 MPa | Compression applied in z direction: 3726 Pa In x or y direction: 453 Pa. Strut thickness 0.3 mm. For 1.0 mm strut thickness, z direction: 21087 Pa; x or y direction: 1554 Pa. |
| OSI Quad ® Max (silanized polyurethane) | 32 Shore A | 458% elongation to break and up to 50% joint width | 2.66 MPa | Compression applied in z direction: 3298 Pa In xory direction: 2592 Pa. Strut thickness 0.4 mm. |

TABLE 2-continued

| Product Name | Shore hardness A | Elongation at break | Tensile strength and tear strength of fully dense material | Compressive modulus of a 3D bioprinted part with rectilinear infill unless noted |
|---|---|---|---|---|
| Aqueon® | 30 Shore A | 450% | 28 kg/cm$^2$ | Not measured. Strut thickness 0.7 mm |

In a non-limiting example, a desired lattice structure (for the soft tissue mimic) is created using a thermosetting elastomer with Shore A hardness between about 20 Shore A and about 50 Shore A measured as per ASTM D 661. The strut size (diameter) is less than or equal to about 2.0 mm, with a spacing between the struts in the planar region (x-y plane) (measured from center to center) of at least about 1 mm with a spacing in the non-planar vertical direction (the thickness direction or z-direction) ranging from 0.2 mm to 1.5 mm.

Compression testing was done to quantify the compressive modulus of the materials listed in Table 2 on a TA Instrument ElectroForce 3200. A linear deflection rate of 0.5 mm/second was applied and the force measured with a load cell. Compression test samples with varying cross-sectional areas and a height of 15 mm were cut from larger 3D printed pieces. The smallest cross-sectional area was 10 mm×12 mm and the largest was 19.4 mm×16.8 mm in cross section. Force data was converted to stress by dividing by the area. The compressive modulus was determined by calculating the slope of the linear elastic portion of the stress strain data.

In an embodiment, for a soft tissue mimic having a 60/60/60 lattice, the compressive modulus may be 2500 pascals to 7500 pascals, preferably 5500 to 7250 pascals. In another embodiment, for a soft tissue mimic with a rectilinear pattern, the compressive modulus may range from 400 pascals to 3000 pascals when measured in a planar direction (x-y plane) and have a compressive modulus of 3000 to 22000 pascals in the thickness direction. Other moduli of exemplary embodiments are found in Table 3.

The materials used to make the soft tissue mimic may include other additives such as pigment, small reflective pieces, antioxidants, antiozonants, flame retardants, and the like. The reflective pieces may comprise metallic, polymeric, ceramic or carbon particulates. The particulates may endow the soft tissue mimic with the ability to change color in response to temperature or light. The additives may also include materials that allow for detection of a particular chemical or salt or protein in body tissues or other items adjacent to the STM. These components within the struts may allow for sensitive measurements of a variety of body functions or chemistries or exposure or contact with certain chemicals.

In some embodiments, the soft tissue mimic as described herein may include at least one sensor. The soft tissue mimic with a sensor as described herein may be a wearable device capable of feedback to the user of such soft tissue mimic and/or may be used for remote monitoring of the user by others. The sensor may be capable of measuring a variety of parameters, including but not limited to, atmospheric data (e.g., temperature, humidity, pressure), user data (e.g., temperature, biomolecular signatures in sweat), and a combination thereof. The soft tissue mimic may be made to function as a faraday cage to prevent transmission of electromagnetic frequency signals.

An extrusion-based direct write 3D printer may be used to build up the soft tissue mimic by deposition of a filament of material that is formed when a material (e.g., an elastomer) in uncured gel form is extruded out of a nozzle attached to a syringe containing the material in uncured gel form. The syringe is guided across the 3D build platform by a computer-controlled extruder to deposit filaments of the gel with the first layer touching the contoured build support. Traditionally, 3D printed parts are built on flat platforms. If there are overhangs of material that extend below/beyond the width of the base of the object being printed, then a support material may be required to support said overhangs. In this case, the part may be co-printed with a support material or printed within a solution of beads.

The exterior outer surface of the breast form, or interior layers, may be printed in a finer pattern, and/or with another material of higher strength to increase mechanical integrity of the part. The finer pattern on the exterior surface would give a smoother appearance and would prevent large infill patterns from showing through thin fabric. The outer surface may also be covered with a fabric to prevent larger infill patterns from showing through a thin fabric. The designs are highly variable, as outlined below and in the attached materials.

The desirability/functionality of the soft tissue mimic (e.g., a desired porosity, mechanical properties) may be defined, at least in part, by the thickness of and/or the spacing of a filament. Oftentimes, and in combination therewith, the desirability/functionality of soft tissue mimic may further be defined by the properties of the filament material. Moreover, the process may provide advantageous mechanical and thermodynamic properties of soft tissue mimics.

The soft tissue mimic may include a lattice structure in a grid-like pattern (hereinafter grid). The grid may include a variety of infill patterns including but not limited to, grid, rectilinear, triangle, herringbone, cylindrical, and honeycomb. These will be detailed later.

The grid comprises a plurality of first struts having an average first direction (an average first orientation) in a first plane (also referred to as a first layer) with an average first spacing. Disposed on the plurality of first struts is a plurality of second struts having an average second direction (an average second orientation) in a second plane (also referred to as a second layer) with an average second spacing. In this manner, pluralities of struts may be disposed in different planes one atop the other to form the soft tissue mimic. In an embodiment, the soft tissue mimic may be viewed as comprising a plurality of n struts arranged in n different planes where each plane has an average orientation in an $n^{th}$ direction with an average $(n-1)^{th}$ spacing between each of struts of the plurality of n struts. In this case "n" is an integer. At least a portion of the struts in each of the n planes contact each other to form the grid. In an embodiment, at least a portion of the struts in each of the planes contact each other directly.

The grid refers to a basic building block that is formed off of the struts and that repeats itself across at least a portion of the soft tissue mimic. In one manner, the grid may be thought of as a repeat unit that repeats itself (translates itself) across a portion of the soft tissue mimic. The grid is also referred to herein as a lattice (since it provides an almost crystalline appearance to the soft tissue mimic). The soft tissue mimic may comprise a plurality of different grids in different regions of the soft tissue mimic. In an embodiment, the soft tissue mimic may comprise a plurality of identically structured grids but the materials used in different grids may be different. In an embodiment, the soft tissue mimic may comprise a plurality of different grids with each of the plurality of grids comprising a different material of construction.

The struts that form the grid may be linear struts, curved struts, wavy struts (having a sinusoidal shape or contour), and the like. They may have a regular shape or an irregular shape. The grid is also referred to as an infill pattern since it is used to fill in the region between the outer surfaces of the soft tissue mimic.

FIGS. 1A and 1B depict a soft tissue mimic 100 that may be used as a replacement for a breast after a patient has undergone a mastectomy. The soft tissue mimic 100 may be manufactured as a single piece or as a two-piece device. While not shown here it is understood that the soft tissue mimic may comprise a multi-piece device, where each piece has the same or different materials of construction, the same or different material properties, and so on. Some of these different embodiments are detailed below.

FIG. 1A depicts the two-piece soft tissue mimic 100 while FIG. 1B depicts the single piece soft tissue mimic 100. FIGS. 1A and 1B depict the side view and the top view of the soft tissue mimic 100. The two piece soft tissue mimic 100 comprises a first piece 104 (also known as a base piece 104) that has one surface 104B that is designed to match with the surface (on the body) that it is being disposed upon. The surface 104B is typically curved (contoured) to closely contact the surface of the body that it will rest upon. The opposing surface 104A is typically flat and is designed to contact a flat surface 102B of the second piece 102. The curved surface 102A of the second piece conforms to the breast of the user as previously scanned. It may also be modified during manufacturing to deviate from the scan and to conform to the desires of the user. The top view of the soft tissue mimic is shown to be elliptical for expediency but in practice will conform to the breast of the user as previously scanned.

FIG. 1B depicts the side view and the top view of a single piece soft tissue mimic 100. With reference to the side view of the soft tissue mimic 106, the lower surface 106B is shaped to mate with the surface of the living being that it will be placed in contact with. The upper surface 106A is curved and conforms to the original or remaining breast of the user as previously scanned. As noted above, it can be further modified according to the desires of the user during manufacturing.

FIG. 1C depicts a two-part soft tissue mimic where two forms of the soft tissue mimic 106 (of the forms depicted in the FIG. 1A or 1B) may be linked together with a spacer (made of 3D printed elastomer) 112. The two soft tissue mimics 106 may each comprise stability flaps 114 extending from the form at the point where the two part forms are glued together. In a two part soft tissue mimic, the flaps 114 may be 3D printed at the bottom layer of one or both forms as an extension of the forms. The purpose of these flaps that extend outwards is that they can be inserted under a bra strap to prevent migration of the forms upwards and out of the bra.

FIG. 2 depicts the extrusion of a filament to form the first piece 104 depicted in the FIG. 1A. The filament 204 emanates from a nozzle 202 of a syringe 200 that contacts a computer-controlled extruder. The motion of the extruder is dictated by the shape of the soft tissue mimic. The first piece is manufactured on a substrate 110 having a flat surface. The flat surface 104A of the first piece 104 is manufactured on the flat surface of the substrate (in the x-y plane) while the contoured surface 104B faces away from the flat surface of the substrate. The thickness of the first piece varies according to the contoured surface in the z-direction. As noted above, the contoured surface corresponds to a surface of the user's body that has had a portion removed.

In an embodiment, the second piece 102 can be manufactured after the first piece 104. The two pieces (the first piece 104 and the second piece 102) can then be placed on the body of the patient and held in position by a garment (e.g., a brassiere). The single piece soft tissue mimic 106 can be manufactured in a one-step process in a manner similar to the manufacturing of the first piece 104 or the second piece. The manufacturing of these pieces 102, 104 and 106 is detailed below.

As detailed above, the respective pieces of the soft tissue mimic are manufactured via extrusion of an elastomeric filament from an extrusion-based direct write 3D printer. In one embodiment, the 3D printer produces the soft tissue mimic by laying down a plurality of filaments that undergo crosslinking to form struts.

In one embodiment depicted in the FIG. 3, a first plurality of struts 206A, 206A', 206A", and so on are extruded from the nozzle in a first direction on a non-stick substrate (not shown). The first plurality of struts are extruded in a first plane 302. The plurality of struts disposed in the first plane 302 are also referred to as a layer of struts. FIG. 3 depicts the sequential buildup of the soft tissue mimic by depositing sequential layers of struts. The arrows indicate the deposition of sequential layers of struts during the process. The FIG. 3 depicts the side view (x-z plane) and the top view (x-y plane) for each layer of struts that are added during the manufacturing. While the FIG. 3 depicts the deposition of only 3 layers, a larger number of layers may be used to form the soft tissue mimic. The soft tissue mimic can include 10 or more layers, 20 or more layers, 50 or more layers, 100 or more layers of struts, and so on. The number of layers added depends upon the thickness of the soft tissue mimic, the diameter of the filaments and the spacing between the filaments in the successive layers of struts in the z-direction. In an embodiment, the soft tissue mimic can have n layers, where n is an integer. The n layers will have n–1 spacings between them. In an embodiment, n is equal to 1, 2, 3, 4, 5 or more, 10 or more, 20 or more, 30 or more, and so on upto 100 or more.

A second plurality of struts (208A, 208A', 208A", and so on) (also referred to as a second layer of struts) is then laid down on top of the first plurality of struts in a second direction that is different from the first direction. The second plurality of struts directly contact at least a portion of the first plurality of struts. The second direction is inclined at an angle θ to the first direction. The second plurality of struts do not dip down into the spaces in between the first plurality of struts. In other words, each strut of second plurality of struts lies in a second plane 304 that is parallel to the first plane 302 that contains the first plurality of struts. During the deposition of the second plurality of struts, the nozzle from the 3D printer is moved at a speed such that the filament does not move or displace the previously deposited struts in plane 302. The extrudate also emerges from the nozzle at a viscosity and velocity that prevents it from dipping into the spaces between the struts 206A, 206A', 206A" of the first layer.

The angle $\theta_1$ can vary from 5 degrees to 175 degrees, preferably 60 to 120 degrees, and preferably 75 to 105 degrees. When $\theta_1$ is 90 degrees the areal space between struts (in two different planes—e.g., plane 302 and plane 304) may appear to be a square or a rectangle when viewed from the top. Such a structure is sometimes referred to herein as a rectilinear structure.

A third plurality of struts (210A, 210A', 210A", and so on) is then laid down in a third direction that is either the same or different from that of the first plurality of struts or from the second plurality of struts. The third plurality of struts directly contacts at least a portion of the second plurality of struts. The third direction is at an angle $\theta_2$ with respect to the second direction. The third plurality of struts lies in a plane 306 that is parallel to planes 302 and 304. The angle $\theta_2$ can vary from 5 degrees to 175 degrees, preferably 60 to 120 degrees, and preferably 75 to 105 degrees. When $\theta_2$ is 90 degrees the areal space between struts (in two different planes—e.g., plane 302 and plane 304) may appear to be a square or a rectangle when viewed from the top. In an embodiment, $\theta_2$ is equal to $\theta_1$. In other words, the struts in the odd numbered layers (the first layer, the third layer, the fifth layer, and so on) all lie in one direction (a first direction), while the struts in the even numbered layers (the second layer, the fourth layer, the sixth layer, and so on) all lie in the same direction (a second direction that is different from the first direction).

In this manner, successive pluralities of struts may be added to each preceding plurality of struts. By placing each successive plurality of struts in a different direction from the preceding plurality of struts, a 3D lattice or grid is built up. The resulting structure is light weight and porous and is sometimes referred to as a "bridging" structure because the struts in alternative layers act as a bridge to contact struts in neighboring layers. In another embodiment, the soft tissue mimic may be manufactured from multiple parts with different x-y planes and then glued together so that the x-y plane of one piece is glued to the x-y plane of another. In this manner, the soft tissue mimic may be manufactured in a series of pieces that can be assembled together and held together by an adhesive. In another embodiment, one piece may be connected to another piece via velcro or via mechanical friction such as by using dove tail joints, and the like.

In an embodiment, with regard to the FIG. 3, it may be seen that the successive neighboring struts in any particular layer (of struts) are periodically spaced. Struts in a particular layer may have the same or different periodicity as the struts in a preceding layer. In an embodiment, the entire soft tissue mimic may have struts that are periodically arranged. In another embodiment, the struts in odd numbered layers may have a first periodicity, while the struts in even numbered layers may have a second periodicity that is different from the first periodicity. The spacing between struts may therefore have a unimodal, bimodal, trimodal, and so on up to an "n−1" modal distribution of strut spacings in the soft tissue mimic, where n is an integer that can have any value from 1 to the total number of strut layers "n" in the soft tissue mimic.

In an embodiment, the struts throughout the soft tissue mimic may all have identical diameters. Alternatively, different layers of struts may have diameters that are different from struts in a neighboring layer. In an embodiment, the struts in odd numbered layers may have a first diameter, while the struts in even numbered layers may have a second diameter that is the same or different from the first diameter. In other words, there may be a unimodal, bimodal, trimodal, and so on upto an "n" modal distribution of strut diameters in the soft tissue mimic, where n is an integer that can have any value from 1 to the total number of strut layers "n" in the soft tissue mimic.

FIG. 4 depicts another embodiment by which the soft tissue mimic may be manufactured. In this embodiment, the first plurality of struts 206A, 206A', 206" and so on, and the second plurality of struts 208A, 208A', 208A", and so on, lie in the first plane 302. The first plurality of struts may be inclined at an angle $\theta_1$ with regard to the second plurality of struts. The third plurality of struts 201A, 201A', 210A", and so on, along with the fourth plurality of struts (not shown) lie in a second plane 304, which is parallel to the first plane 304. The third plurality of struts may be inclined at an angle $\theta_2$ with regard to the second plurality of struts. The angles for $\theta_1$ and $\theta_2$ are provided above and will not be repeated again in the interests of brevity. The soft tissue mimic produced by this arrangement is more compact than the structure depicted in the FIG. 3 and has a higher density, with smaller pores (when filament size in both structures is retained at the same value). This sample is referred to as a "non-bridging" sample because there are no struts that act as a bridge between two adjacent struts.

With reference now to the FIGS. 3 and 4, in an embodiment, each succeeding layer of struts are disposed on the preceding layer of struts such that individual struts in a plane are disposed atop individual struts in a preceding plane leading to the formation of walls in the thickness direction. For example, in the FIGS. 3 and 4 each strut of the third plurality of struts are disposed either directly over or slightly offset from each strut of the first plurality of struts. Each strut of the fourth plurality of struts are disposed either directly over or slightly offset from each strut of the second plurality of struts. This leads to the formation of walls in a plane that is different from the first plane and the second plane. The walls are formed in the thickness direction and may be inclined at angles of 5 degrees to 175 degrees with respect to the first plane and/or the second plane. In an embodiment, the walls are inclined at an angle of about 90 degrees with regard to the first plane or the second plane. This would occur when $\theta_1=\theta_2=90$ degrees in the FIGS. 3 and 4 and the struts in alternating planes are directly disposed one atop the other.

FIGS. 5A and 5B depict embodiments where there is a multimodal distribution in spacing between struts in at least one layer (of struts) in the soft tissue mimic. FIG. 5A depicts a top view of one layer of the soft tissue mimic where the first spacing between neighboring struts 410A and 410A' (and between 410B and 410B', 410C and 410C', and 410D and 410D') is different from the second spacing between 410A and 410B (as well as between 410B and 410C or between 410C and 410D). The first spacing and the second spacing are different from the third spacing between neighboring struts 412A, 412A', 412A" and 412A'". By using a different spacing between the struts in one or more layers of the soft tissue mimic, soft tissue mimics with different properties can be manufactured. For example, properties such as the compressive or tensile properties or the tactile feel of the soft tissue mimic can be changed by adding one or more layers with a different spacing between neighboring struts.

FIG. 5B depicts one embodiment where there is a first spacing between struts in one portion of the soft tissue mimic while there is a different spacing between struts in another portion of the soft tissue mimic. FIG. 5B reflects a top view of one layer of the soft tissue mimic where the density of struts in region 600 are greater than the density of struts in region 700. The spacing between the struts in region 600 is lower than the spacing of struts in the region 700. These variations may be used to tailor properties of the soft tissue mimic depending upon user preferences.

In one embodiment, the density of filaments on an outer surface of the soft tissue mimic may be different (greater or less) than the density of filaments in the interior of the soft tissue mimic. When the density of struts on the outer surface is greater than the density of struts in the interior of the soft tissue mimic, the outer surface has a greater compressive strength than the inner regions of the soft tissue mimic. This type of variation may also occur in the interior of the soft tissue mimic.

In an embodiment, certain selected layers (of struts) in the interior or exterior of the soft tissue mimic may have a greater strut density than other layers in the interior or exterior of the soft tissue mimic. In another embodiment, portions of the soft tissue mimic may contain 75% or less, preferably 50% or less of the struts contained in other portions of the soft tissue mimic.

FIG. 5C details an exemplary soft tissue mimic 630 (shown in top view only) which comprises regions of different strut densities—a first region 612 having a first strut density, a second region 614 having a second density and a third region 616 having a third strut density. By combining regions having different strut densities different regions of the soft tissue mimic will have different compressive strengths providing the user with soft tissue mimic having a different tactile feel in different regions. In addition, the FIG. 5C depicts one layer of struts 618 in a first direction and another layer of struts 620 in a second direction where the struts have a different diameter (the diameter is larger) from the surrounding struts. Thus, by using struts of different sizes in a single soft tissue mimic reinforcement can be provided to certain regions or planes of the soft tissue mimic to prevent the soft tissue mimic from buckling or folding in certain regions. The elasticity and stiffness of the soft tissue mimic can be varied by providing the soft tissue mimic with regions of different strut densities and/or by providing the soft tissue mimic with planes of struts having a different thickness from those of the surrounding struts.

FIG. 5D details another exemplary soft tissue mimic (shown in top view only) 640 which comprises regions having different grid designs and different strut densities. Region 642 contains struts in two different directions (having a first strut density) while region 644 contains struts in three different directions (having a second strut density). The grid in the region 642 comprises squares while the grid in the region 644 comprises triangles. The grid design containing triangles is detailed below in the FIG. 8. The first strut density can be the same or different from the second strut density. The different grid structures of 642 and 644 may also have been 3D printed as separate pieces and then rotated and then glued together. In an embodiment the x-z plane or z-y plane of one piece is attached to the x-y plane of a second piece. By manufacturing the soft tissue mimic with regions of different grid structures, different properties such as compressive modulus, force deflection, tactile feel, flexibility, and the like can be imparted to the soft tissue mimic.

FIG. 5E depicts an exemplary soft tissue mimic 760 where a plurality of struts are disposed a plane that is in a different plane from the parallel or perpendicular planes that contain the remaining plurality of struts. FIG. 5E depicts a grid that contains walls 748A, 748B, 748C, and so on (formed from a plurality of first struts that are in the plane of the paper) and walls 750A, 750B, 750C, and so on (formed from a plurality of second struts that are parallel to the plane of the paper). The walls 748A, 748B, 748C . . . and 750A, 750B, 750C, . . . extend outwards from the plane of the paper in the z direction (the thickness direction).

FIG. 5E depicts a macro strut 746 constructed within the grid with is inclined at an angle α to the other planes of the grid (the other planes of the grid are in planes parallel to the plane of the paper). The macro strut is manufactured as a series of smaller steps (similar to a staircase). However, each step is very slightly higher than the preceding step such that to the naked eye, the macro strut appears to be a smooth planar strut that is inclined at an angle α to the walls of the grid. The macro strut extends from the bottom right of the wall 748A to the front top of wall 750F at the angle α, which may vary from 5 degrees to 150 degrees.

The process for formation of a macro strut is shown in the box depicted as section 762. Section 762 encompasses the regions between walls 748F and 748G and 750E and 750F. In order to form the macro-strut, additional struts 748F1 and 748F2 as well as 750E1 and 750E2 are deposited in small areas in each plane of the larger grid. There is a smaller spacing between the struts 748F1 and 748F2 or between 750E1 and 750E2 that between the struts that forms walls 748A and 748B or between 750A and 750B. The repetitive deposition of these struts between successive grids produces the macro strut 746. The smaller spacing between the struts that form the macro strut 746 (than the spacing between walls 748A and 748B or between 750A and 750B) makes the macro strut 746 more rigid.

FIGS. 5F and 5G depicts one method of manufacturing the macro strut. The macro strut is formed in a staircase like fashion as represented by the macro strut portions M, N, O, P, Q and R as seen in the FIGS. 5F and 5G. Macro strut M is manufactured first and is located in the lower right hand corner of the grid while macro strut R is manufactured last and is located in the upper left hand corner of the grid. The remaining macro struts N, O, P and Q are each located in higher planes than the preceding plane to create a step like appearance. The vertical distance between successive macro struts M, N, O, P, Q and R is so small however, that when viewed from the side or the front, it appears that the macro strut 746 is inclined at an angle α to the walls 748A and 750A. (See FIG. 5G)

The macro strut 746 is provides the soft tissue mimic with reinforcement and support to prevent it from deforming or folding in an undesirable manner. In an embodiment, the macro strut 746 is constructed in a plane that is perpendicular to the walls 748 and second struts 750 and provides the soft tissue mimic with reinforcement and support to prevent it from deforming or folding in an undesirable manner.

While the FIGS. 3, 4, 5A, 5B, 5C and 5D depict struts that are linear in shape, the struts can be curvilinear or wavy in shape as desired. In an embodiment, the wavy struts have a shape that is sinusoidal. For example, the struts in one direction can have a linear shape while the struts in another direction can have a wavy shape.

FIG. 6 depicts linear struts 702A, 702A' and 702A", while struts 602A, 602A' and 602A" (which point in another direction from strut 702A) are wavy (i.e., sinusoidal in shape). In this manner, every strut in the soft tissue mimic can be wavy (not shown) i.e., struts which travel in multiple directions can be wavy. Inter-strut spacing and strut diameters can also be varied as detailed above when a portion of the struts are wavy.

FIG. 7 depicts another embodiment where the soft tissue mimic is manufactured using wavy struts that contact each other at certain points. In this embodiment, the struts 602A, 602A' and 602A" have a shape that is dictated by a sinusoidal wave and contact each other at points such as 604 and 606. By varying the amplitude and phase of the sinusoidal wave as well as by varying the number of contact points between the different struts, soft tissue mimics with different properties can be produced.

FIG. 8 depicts another embodiment, in which the soft tissue mimic comprises 3 pluralities of struts 608, 610 and 612. The first plurality of struts 612 is inclined at an angle of $\theta_1=45$ to 75 degrees, preferably 60 degrees with regard to the second plurality of struts 608 and at an angle of $\theta_2=45$ to 75 degrees, preferably 60 degrees with regard to the third plurality of struts 612. Each plurality of struts comprises individual struts parallel to each other and each plurality of struts may lie in a different plane from a neighboring plurality of struts (see FIG. 3) or in the same plane as the neighboring plurality of struts (see FIG. 4). The second plurality of struts 608 is inclined at an angle of $\theta_3=45$ to 75 degrees, preferably 60 degrees with regard to the third plurality of struts 612. The resulting grid from this arrangement has lattice that appears to be triangular when the struts are spaced equally. When $\theta_1=\theta_2=\theta_3=60$ degrees, the triangular lattice comprises an equilateral triangle. With other angles, the triangular lattice can comprise isosceles triangles or right-angled triangles. The lattice can also include honeycomb structures.

In an embodiment, the outer surface of the soft tissue mimic may have a pattern disposed on its outer surface for decorative purposes (not shown). The pattern may be provided to enhance the appearance of the soft tissue mimic or to facilitate adhesion of the soft tissue mimic to undergarments (e.g., a brassiere).

In another embodiment, a portion of the soft tissue mimic may have a different density from the rest of the soft tissue mimic. This could be accomplished by printing around a dense material or printing the dense material at the time the rest of the soft tissue mimic is printed. FIG. 9A depicts a portion of the soft tissue mimic 106 (having upper surface 106A and contoured lower surface 106B) which has certain volume of the soft tissue mimic made with a material 107 having a different density than the rest of the soft tissue mimic. FIG. 9A is another embodiment of the FIG. 1B, where the soft tissue mimic comprises only a plurality of struts. The plurality of struts from the FIG. 1B can comprise a first elastomer. The material 107 may comprise the first elastomer (or may comprise a second elastomer that has a different chemical composition from the first elastomer) but may have a different density from the rest of the soft tissue mimic. By providing void space for materials of a greater density or printing areas of higher density in the soft tissue mimic, the soft tissue mimic can be made to behave in a manner similar to naturally occurring breast tissue. The deformation of the outer portion of the soft tissue mimic may move more than the portion of the soft tissue mimic closest to the body. In an embodiment, both the plurality of struts used to form the soft tissue mimic 106 of the FIG. 9A and the material 107 used in the soft tissue mimic 106 may both comprise a polysiloxane. In an embodiment, the material 107 may be a solid polysiloxane not 3D printed at the time of printing the grid. In another embodiment, the material 107 may comprise a plurality of struts having a different density from the plurality of struts used in the remainder of the soft tissue mimic 106.

In another embodiment, the material 107 may be a void that is filled with ambient air. A soft tissue mimic 106 may comprise a plurality of such voids to increase breathability to the soft tissue mimic.

In an embodiment, seen in the FIG. 9B the soft tissue mimic may comprise two regions 700 and 800 that have a similar structure (i.e., both contain struts of the same diameter and spacing) but contain two different materials of construction. The region 700 may comprise a first material (e.g., a polysiloxane) while the region 800 may comprise a second material (e.g., a silanized polyurethane). The different regions may be compatible with one another (and may not need to be adhesively bonded to each other) or alternatively, may be adhesively bonded to each other.

In an embodiment, the upper region or lower region may be 3D printed around a pre-printed lattice made of another material 108 that may be a thermoplastic polyurethane (TPU) printed separately using a fused deposition modeling printer rather than a laminar flow extrusion direct write printer.

In FIG. 9C, the design may include larger pores or channels 109 (than those in the grid) that allow for more rapid water exit when the soft tissue mimic is immersed in water. The directionality of those larger through pores would allow water to exit when the user is standing in a vertical position. In an embodiment, the direction of the pores may allow for the water to exit irrespective of the posture of the user.

FIG. 9D depicts another embodiment of a soft tissue mimic 220 that contains solid ribs 107 that extend radially outwards from a central 210. The solid ribs 107 contact a grid 207. The presence of the ribs within the grid structure provide bridge-like reinforcement to the soft tissue mimic. In one embodiment, the grid extends between the solid ribs. In another embodiment, the ribs are located within the grid and may be covered by the grid. The solid ribs 107 may be formed during the printing of the soft tissue mimic 220. In another embodiment, the solid ribs 107 may be independently manufactured prior to the printing of the grid.

The struts that make up the lattice structure (the grid) may have an average diameter of about 0.1 millimeters (mm) to about 4.0 mm, preferably 0.2 to 3.0 mm and more preferably about 0.3 mm to about 2.0 mm. The strut spacing is an average spacing may be between about 0.5 mm to about 10.0 mm planar to the soft tissue mimic (for example, in the x-y plane, x-z plane, y-z plane). The strut spacing in a direction outward from the plane of the soft tissue mimic (for example, z-direction when the x-y plane is used; the y-direction when the x-z plane is used, the x direction when the y-z plane is used) may be about 0.1 mm to about 4.0 mm for a strut with a diameter of about 0.1 mm to about 3.0 mm. It should be understood that the volume fraction (e.g., the strut spacing, strut diameter) may be varied. As detailed above, the varying of the volume fraction may change the rigidity of the lattice structure. As used herein, the spacing of the strut is measured between the edges of the strut. However, the strut spacing may be measured from the center of the strut, without departing from the spirit/scope of this disclosure. In an exemplary embodiment, the spacing of the strut is measured between the edges of the struts. In an embodiment, all of the strut diameters and strut spacings are average spacings. The orientations of the struts and planes (layers) disclosed herein may be average orientations.

In an exemplary embodiment, a rectilinear pattern may be printed with layers in the x-y plane with a height in the z-direction. In an embodiment, the soft tissue mimic may be more compressible in one direction (in the x-y plane) than in another direction (in the z-direction). It should also be understood that the directionality of the openings of the lattice structure can be varied to change the mechanical properties. For example, the mechanical properties as perceived in the desired orientation with regard to a patient's body.

In an embodiment, an adhesive may be applied to the soft tissue mimic for attachment to a surface of the body. Otherwise, the porous elastomeric structure is somewhat self-bonding to skin, particularly when lightly compressed by a clothing article such a brassiere or swimsuit or sock or body sculpting undergarments. Tabs or stability flaps may extend from the soft tissue mimic that can be tucked under the bands of undergarments.

In an embodiment, when the soft tissue mimic formed herein is to be used as a prosthetic, it may be disposed in a thin film of an elastomeric material. In an embodiment, the thin film may be only applied to the lattice work. The elastomeric material that forms the film is generally 0.1 micrometer to 50 micrometers, preferably 0.2 to 20 micrometers, and more preferably 0.5 to 10 micrometers thick. The elastomeric material used for the film may comprise a polysiloxane, a fluoropolymer, polyurethane, a silanized polyurethane, or the like, or a combination thereof. The elastomeric material used for the film is preferably biocompatible. The film may contain a layer of a barrier material that prevents ingress of body fluids into the prosthetic.

In one embodiment, the lattice structure as defined herein can be used as bandages. For example, if made into the breast shape of the woman, the bandages may be used over the top of traditionally bandaged mastectomy surgery areas. The structure may be made into a tape form that could be used for a variety of purposes anywhere a porous tape or flexible netting may be needed.

The soft tissue mimic disclosed herein and the method of manufacturing of the soft tissue mimic is exemplified by the following non-limiting example.

EXAMPLE

Example 1

This example was conducted to demonstrate that the soft tissue mimic can be manufactured by a 3D laminar flow extrusion/direct write printer from a variety of different thermosetting elastomers. FIG. 10 illustrates printed lattice structures manufactured from three materials with varying patterns and strut thicknesses. Sample #s 1 to 5 are arranged in the FIG. 10 from left to right. The samples along with the materials that they are manufactured from are detailed below.

Sample #1 refers to PCI Silcoferm® printed with an EnvisionTEC Bioplotter.

Sample #2 refers to PCI Silcoferm® printed with a thick structure on the Cellink® BioX. Sample #3 refers to OSI Quad® Max printed with a Cellink® BioX;

Sample #4 refers to a 45 degree cross-section of Sample #3; and

Sample #5 refers to Dowsil™ SE1700 and Sylgard™ 184 mixture printed with a ASLS Bioassembly Bot 400.

The materials from which the Sample #s 1 to 5 are manufactured are listed in Tables 1 and 2 above.

Example 2

This example was conducted to demonstrate some of the properties of a soft tissue mimic.

Samples were 3D printed with a triangular lattice structure to the specified dimensions of 50 mm×50 mm×25 mm (L×W×H). The compression testing of the samples is conducted using ASTM D 3574 Test C. This is a compression force deflection test. Compressive force deflection and compressive modulus were measured. In this test two compression pre-cycles were conducted at 250 mm/min to a setpoint of 75% of the thickness followed by a compression to 50% thickness at 50 mm/min. The reportable data is the final stress at 50% thickness. The compressive modulus at 10% strain is also reported for some of the samples tested. Table 3 shows the test results.

TABLE 3

| Sample | Compressive force deflection, (kPa) | Compressive Modulus (kPa) |
|---|---|---|
| U1B-18GA-3 mm | 16.26 | — |
| U1B-18GA-4 mm | 5.18 | 37 |
| U1B-22GA-2 mm | 8.98 | — |
| U1B-22Ga-3 mm | 2.54 | — |
| U1B-22Ga-4 mm | 1.29 | 11 |
| U1B-22Ga-8 mm | 0.37 | 7 |
| U1NB-18Ga-3 mm | 95.61 | — |
| U1NB-18Ga-4 mm | 40.3 | — |
| U1NB-22Ga-2 mm | 64.39 | 240 |
| U1NB-22Ga-3 mm | 20.1 | — |
| U1NB-22Ga-4 mm | 15.66 | — |
| U1NB-22Ga-8 mm | 2.88 | — |
| S2B-22Ga-4 mm | 1.3 | — |
| U1B-18Ga-2 mm | 52.8 | — |
| U1B-20Ga-2 mm | 23.3 | — |
| U1NB-18Ga-2 mm | 323.9 | 241 |
| U1NB-18Ga-8 mm | 16.6 | — |
| U1NB-20Ga-2 mm | 265.5 | — |
| U1NB-20Ga-8 mm | 9.6 | — |

The nomenclature used in the Table 3 above is as follows. U1 indicates that the samples were manufactured from a silanized urethane called QuadMax, also tested in Table 2. S2 indicates that the samples were manufactured from a polysiloxane obtained from Kason Rubbaseal. B indicates that the samples were bridging samples (see FIG. 3 for a description of bridging samples), while NB indicates that the samples were non-bridging samples (see FIG. 4 for a description of non-bridging samples). The number that precedes the letters GA indicates the gauge (diameter) of the nozzle used during 3D printing. The last number (e.g., 3 mm) is the filament spacing in the x-y plane (center to center filament spacing) specified by the 3D printer software.

The compressive force deflection is measured in kilopascals (kPa). In an embodiment, the compressive force deflection values may be 0.2 kPa to 600 kPa, or more specifically 0.4 to 330 kPa. The wider the filament spacing, the softer the samples (compare U1B-22GA 2, 3, 4 mm). The soft tissue mimic with the non-bridging structure has a higher compressive force deflection compared with the samples that have the bridging structure for the same filament gauge and filament spacing (non-bridged vs bridged –18 gauge nozzle with 4 mm spacing). The use of a larger nozzle (18 gauge vs 22 gauge) result in a thicker filament and a stronger structure (compare U1NB-18Ga vs 22 Ga both with 4 mm spacing).

In an embodiment, the compressive modulus varies from 1 to 350 kPa, in an exemplary embodiment the compression modulus varies from 10 to 150 kPa.

As used herein, "a", "an", and "the" refer to both singular and plural referents unless the context clearly dictates otherwise.

As used herein, the term "about" refers to a measurable value such as a parameter, an amount, a temporal duration, and the like and is meant to include variations of +/−15% or less, preferably variations of +/−10% or less, more preferably variations of +/−5% or less, even more preferably variations of +/−1% or less, and still more preferably variations of +/−0.1% or less of and from the particularly recited value, in so far as such variations are appropriate to perform in the invention described herein. Furthermore, it is also to be understood that the value to which the modifier "about" refers is itself specifically disclosed herein.

As used herein, spatially relative terms, such as "beneath", "below", "lower", "above", "upper", "front", "back", "side", "left", "right", "rear", and the like, are used for ease of description to describe one element or feature's relationship to another element(s) or feature(s). It is further understood that the terms "front", "back", "left", and "right" are not intended to be limiting and are intended to be interchangeable, where appropriate. Further, it should be noted that the terms "first," "second," and the like herein do not denote any order, quantity, or relative importance, but rather are used to distinguish one element from another.

As used herein, the terms "comprise(s)", "comprising", and the like, specify the presence of stated features, integers, steps, operations, elements, and/or components, but do not preclude the presence or addition of one or more other features, integers, steps, operations, elements, components, and/or groups thereof.

As used herein, the terms "configure(s)", "configuring", and the like, refer to the capability of a component and/or assembly, but do not preclude the presence or addition of other capabilities, features, components, elements, operations, and any combinations thereof.

As used herein, the terms "filament" and "strand", and the like refer to the material being used to produce the extrusion-based direct write 3D printed soft tissue mimic and these terms may be used interchangeably.

Chemical compounds are described using standard nomenclature. For example, any position not substituted by any indicated group is understood to have its valency filled by a bond as indicated, or a by hydrogen atom.

All ranges disclosed herein are inclusive of the endpoints, and the endpoints are independently combinable with each other. Each range disclosed herein constitutes a disclosure of any point or sub-range lying within the disclosed range.

All methods described herein can be performed in any suitable order unless otherwise indicated herein or otherwise clearly contradicted by context. The use of any and all examples, or exemplary language (e.g., "such as"), is intended merely to better illustrate the invention and does not pose a limitation on the scope of the invention or any embodiments unless otherwise claimed.

Any combination or permutation of features, functions and/or embodiments as disclosed herein is envisioned. Additional advantageous features, functions and applications of the disclosed systems, methods and assemblies of the present disclosure will be apparent from the description which follows, particularly when read in conjunction with the appended figures. All references listed in this disclosure are hereby incorporated by reference in their entireties.

While the invention has been described with reference to preferred embodiments, it will be understood by those skilled in the art that various changes may be made, and equivalents may be substituted for the elements thereof without departing from the scope of the invention. In addition, many modifications may be made to adapt the teaching of the invention to particular use, application, manufacturing conditions, use conditions, composition, medium, size, and/or materials without departing from the essential scope and spirit of the invention. Therefore, it is intended that the invention is not limited to the exemplary embodiments and best mode contemplated for carrying out this invention as described herein. Since many modifications, variations, and changes in detail can be made to the described examples, it is intended that all matters in the preceding description and shown in the accompanying figures be interpreted as illustrative and not in a limiting sense.

What is claimed is:

1. A prosthetic comprising:
   a first surface; and
   a second surface oppositely disposed to the first surface;
      where a space between the first surface and the second surface comprises a grid that comprises:
   a plurality of first struts that have an average orientation in a first direction in a first plane with a first average spacing between neighboring struts of the plurality of first struts; wherein the plurality of first struts comprise 1-dimensional filaments; and
   a plurality of second struts that have an average orientation in a second direction in a second plane with a second average spacing between neighboring struts of the plurality of second struts; where the first direction is different from the second direction;
   a plurality of third struts that have an average orientation in a third direction in a third plane with a third average spacing between neighboring struts of the third struts; wherein a portion of the plurality of third struts contacts either the portion of the plurality of first struts and a portion of the plurality of second struts; wherein the third plane is different from the second plane and the first plane and is oriented in the third average direction to provide reinforcement to the prosthetic;
   and wherein the prosthetic is a two-piece device; where each piece of the two piece device comprises the grid and wherein the first surface of the prosthetic contacts a user's body and is contoured to a surface of the user's body.

2. The prosthetic of claim 1, further comprising a plurality of $n^{th}$ struts that have an average orientation in a $n^{th}$ direction in a $n^{th}$ plane with a $n^{th}$ average spacing between neighboring struts of the first struts; where n is an integer.

3. The prosthetic of claim 2, wherein at least one of the $n^{th}$ planes is not parallel to the first plane and the second plane and wherein strut spacing in the at least one of the $n^{th}$ planes is smaller than strut spacing in the first plane and the second planes.

4. The prosthetic of claim 1, wherein the first plane is parallel to the second plane.

5. The prosthetic of claim 1, wherein the first plane is the same as the second plane.

6. The prosthetic of claim 1, wherein an angle between the first direction and the second direction is 5 to 175 degrees.

7. The prosthetic of claim 1, wherein an angle between the first direction and the second direction is 60 to 120 degrees.

8. The prosthetic of claim 1, wherein the first average spacing is the same as the second average spacing.

9. The prosthetic of claim 1, wherein the first average spacing is different from the second average spacing.

10. The prosthetic of claim 1, wherein the third plane is different from the second plane.

11. The prosthetic of claim 1, wherein an angle between the first average direction and the second average direction is 45 to 75 degrees, wherein an angle between the second average direction and the third average direction is 45 to 75 degrees, and wherein an angle between the first average direction and the third average direction is 45 to 75 degrees.

12. The prosthetic of claim 1, wherein the plurality of first struts, the plurality of second struts, and the plurality of third struts comprise a polymeric elastomer.

13. The prosthetic of claim 12, wherein the polymeric elastomer comprises a polysiloxane, a polyurethane, a thermoplastic polyurethane, a fluoroelastomer, a silanized polyurethane, or a combination thereof.

14. The prosthetic of claim 13, wherein the plurality of first struts, the plurality of second struts and the plurality of third struts have average diameters of 0.1 to 4.0 millimeters.

15. The prosthetic of claim 1, wherein a first piece is adhesively bonded to a second piece in the two-piece device.

16. The prosthetic of claim 1, wherein the prosthetic is a multi-piece device.

17. The prosthetic of claim 1, wherein the grid in a first region comprises a different strut density from a grid in a second region of the prosthetic.

18. The prosthetic of claim 1, wherein the grid in a first region comprises a different material from a grid in a second region of the prosthetic.

19. The prosthetic of claim 1, wherein the prosthetic further comprises a void space that is filled with a solid non-porous material.

20. The prosthetic of claim 1, wherein the prosthetic comprises channels for draining fluids.

21. The prosthetic of claim 1, wherein the first surface is contoured to contact a patient's body.

22. The prosthetic of claim 1, wherein the prosthetic is a soft tissue mimic.

* * * * *